United States Patent [19]

Mihara et al.

[11] Patent Number: 4,568,545

[45] Date of Patent: Feb. 4, 1986

[54] THROMBOLYTIC AGENT

[75] Inventors: Hisashi Mihara, 2754-15, Hongominamikata, Miyazaki-shi, Miyazaki-ken; Hiroyuki Sumi, Miyazaki; Akira Matsuura, Kasugai; Tadahiko Inukai, Nagoya, all of Japan

[73] Assignees: Amano Seiyaku Kabushiki Kaisha, Aichi; Hisashi Mihara, Miyazaki, both of Japan

[21] Appl. No.: 508,163

[22] Filed: Jun. 27, 1983

[30] Foreign Application Priority Data

Oct. 2, 1982 [JP] Japan .............................. 57-173669
Mar. 31, 1983 [JP] Japan .............................. 58-55460

[51] Int. Cl.[4] .................. A61K 37/54; C12N 9/48; C12N 9/64
[52] U.S. Cl. ...................................... 424/94; 435/212; 435/226; 514/822
[58] Field of Search .................... 435/212, 226; 424/94

[56] References Cited

U.S. PATENT DOCUMENTS 4,390,630  6/1983  Sawyer ............................... 435/226

FOREIGN PATENT DOCUMENTS 2116565  9/1983  United Kingdom ............... 435/226

Primary Examiner—Lionel M. Shapiro
Attorney, Agent, or Firm—Brisebois & Kruger

[57] ABSTRACT

The invention discloses that the tissues of earthworms contain fibrinolytically or thrombolytically active ingredients which can be extracted and purified by a suitable sequence of extraction and purification procedures into the individual active ingredients including six novel proteases named F-O-HM-45, F-I-1-HM-54, F-I-2-HM-15, F-II-HM-64, F-III-1-HM-27 and F-III-2-HM-89. The chromatographic fractionation of the earthworm extract with an aqueous extractant gives five active fractions, the first four of which contain each one of the first mentioned four proteases and the last of which contains the last mentioned two proteases. The disclosure includes description of the suitable purification methods for the proteases as well as the physicochemical identification data thereof. Various thrombolytic medicament forms prepared with the novel proteases as the effective ingredient are described together with the results of the clinical tests carried out by the oral administration of the novel proteases.

15 Claims, 48 Drawing Figures

THROMBOLYTIC AGENT

BACKGROUND OF THE INVENTION

The present invention relates to a novel thrombolytic agent comprising, as an effective ingredient thereof, at least one protease selected from the group consisting of protease F-III-1-HM-27 (referred to as HM-27 hereinafter), protease F-III-2-HM-89 (referred to as HM-89 hereinafter), protease F-0-HM-45 (referred to as HM-45 hereinafter), protease F-I-1-HM-54 (referred to as HM-54 hereinafter), protease F-I-2-HM-15 (referred to as HM-15 hereinafter), protease F-II-HM-64 (referred to as HM-64 hereinafter), protease F-III[1], protease F-II[1], protease F-I[1] and protease F-I[2]. Each of these proteases is a white amorphous powder obtained by purifying the extracted material from the tissues of earthworms belonging to the family of Lumbricidae such as Lumbricus rebellus and characterized by the activity of dissolving fibrin, i.e. fibrinolytic activity, and an activity of dissolving thrombi. Such an effective ingredient is not described in any prior art literatures.

Among the above named proteases, the HM-27, HM-89, HM-45, HM-54, HM-15 and HM-64 are each a purified protease of a single component while the proteases F-III[1], F-II[1], F-I[1] and F-I[2] are each a composite composed of two or three kinds of the above named single proteases. That is, protease F-III[1] is a composite of HM-27 and HM-89, protease F-I[1] is a composite of HM-54 and HM-15 and protease F-I[2] is a composite of HM-45, HM-54 and HM-15. Protease F-II[1] is a semi-purified protease mainly composed of HM-64.

These novel proteases can be obtained in a crude form by extracting earthworm tissues with an aqueous extractant solvent at a suitable temperature for a suitable length of time followed by, if necessary, keeping the extract solution for a suitable length of time at a suitable temperature or in a purified form by purifying the above obtained crude products in a known method.

In recent years, attention is directed by the practitioners of medicine and pharmaceutics to various types of the deseases due to the coagulation of blood occurring in many cases of prime and aged adults from the standpoint of geriatrics. Several of the well known deseases of such a type are, for example, myocardinal infarction, cerebral thrombosis, syndrome of disseminated intravascular coagulation and the like and, as is well known, urokinase of man origin and streptokinase are used as a therapeutic medicament therefor.

These medicaments are, however, not quite satisfactory in several respects. For example, urokinase of man origin is prepared from human urine as the starting material so that the supply thereof is limited by the availability of this starting material in large volumes. Streptokinase is defective due to the antigenicity. In addition, both of these medicaments must be used by instillation so that the patient under treatment suffers great pains unavoidably.

Therefore, it has been long desired to develop a novel fibrinolytically active agent usable as a therapeutic medicament of the above mentioned deseases without the problems in the conventional medicaments therefor. That is, one of the recent problems in the pharmaceutics has been to develop a novel fibrinolytically active agent free from the limitation by the availability of the starting material in large quantities and capable of being administrated to the patient not by the instillation but by other means, desirably orally, without giving pains to the patient.

SUMMARY OF THE INVENTION

It is therefore an object of the present invention to provide a novel and effective thrombolytic agent free from the above described problems and disadvantages in the prior art therapeutic medicaments having fibrinolytic or thrombolytic activity. That is, the inventors have continued extensive efforts to find a substance having the above mentioned activity in wide nature and arrived at a discovery that tissues of earthworms contain several proteases having an activity to increase the fibrinolytic activity in the peripheral blood of man resulting in the establishment of the present invention.

Thus, the thrombolytic agent of the present invention comprises, as an effective ingredient thereof, at least one protease selected from the group consisting of the above mentioned proteases HM-27, HM-89, HM-45, HM-54, HM-15 and HM-64 in a therapeutically effective amount and, if necessary, a carrier. This inventive thrombolytic agent is suitable for administration in the form of either an orally administrable medicament or a nonorally administrable medicament but the most preferable medicament form is the orally administrable ones since, as is described later, excellent fibrinolytic or thrombolytic activity is exhibited by the oral administration of the inventive thrombolytic agent to man.

DETAILED DESCRIPTION OF THE PREFERRED EMBODIMENTS

Figure 1:
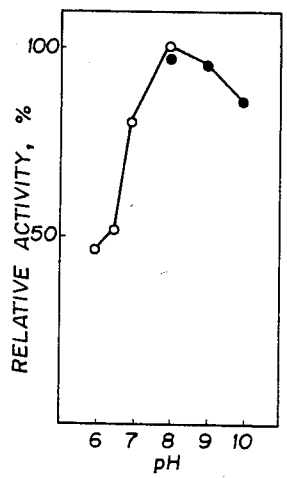
FIGS. 1 to 6 are each a graph showing the relative fibrinolytic activity of the 6 proteases, HM-27, HM-89, HM-45, HM-54, HM-15 and HM-64, respectively, at varied values of pH.
Figure 2:
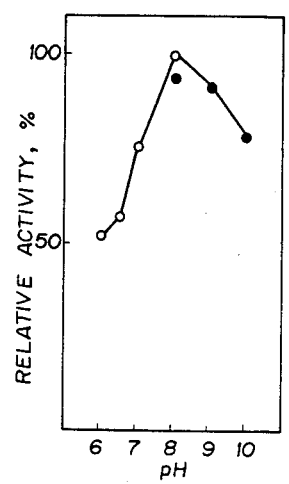
Figure 3:
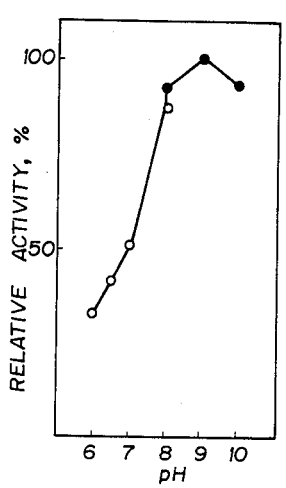
Figure 4:
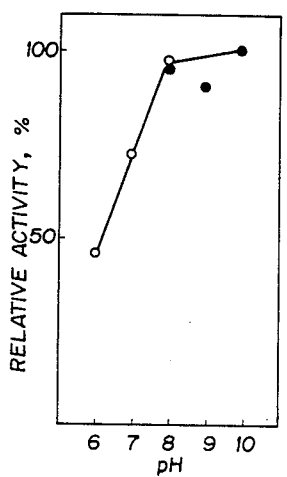
Figure 5:
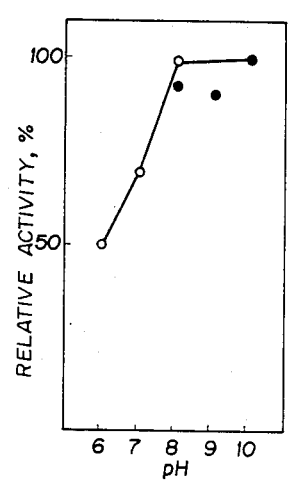
Figure 6:
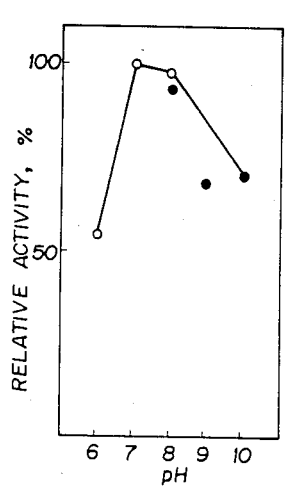
Figure 7:
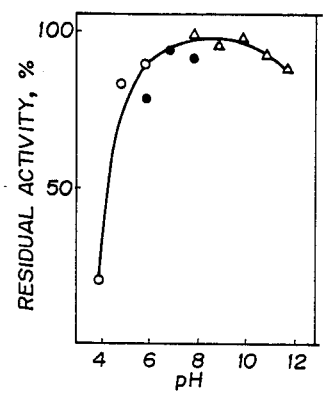
FIGS. 7 to 12 are each a graph showing the residual fibrinolytic activity of the 6 proteases, respectively, at varied values of pH after keeping at 37° C. for 60 minutes.
Figure 8:
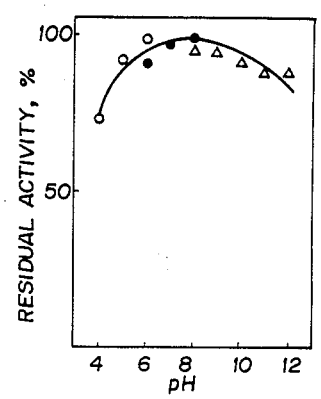
Figure 9:
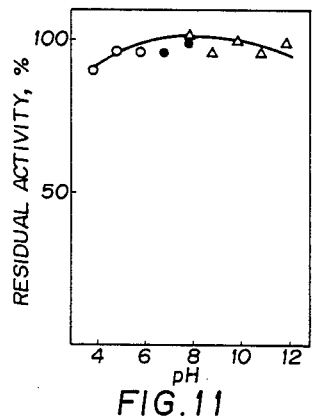
Figure 10:
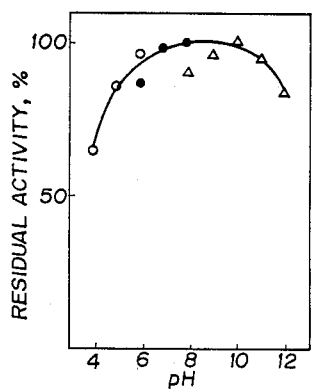
Figure 11:
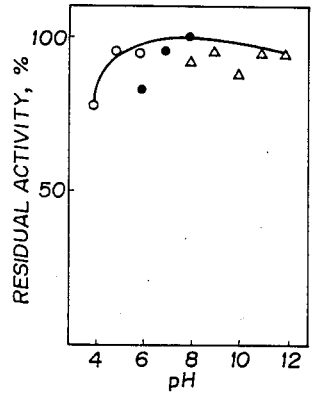
Figure 12:
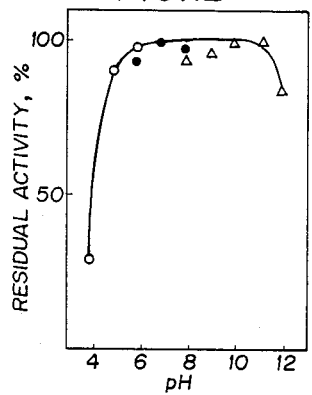
Figure 13:
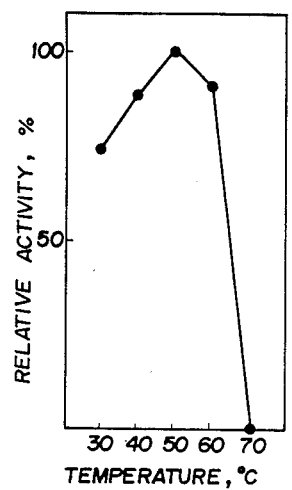
FIGS. 13 to 18 are each a graph showing the relative fibrinolytic activity of the 6 proteases, respectively, as a function of the temperature.
Figure 14:
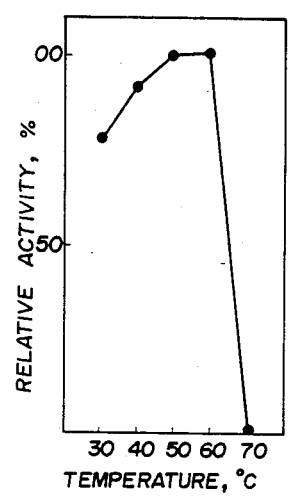
Figure 15:
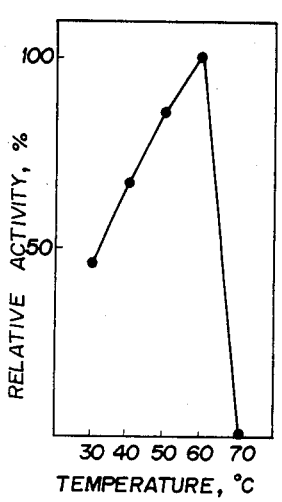
Figure 16:
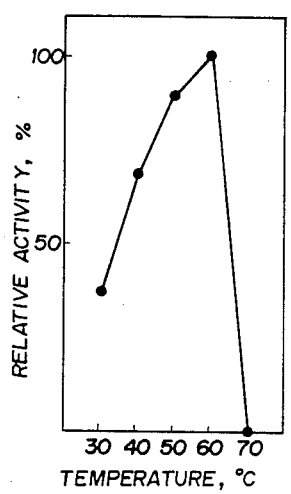
Figure 17:
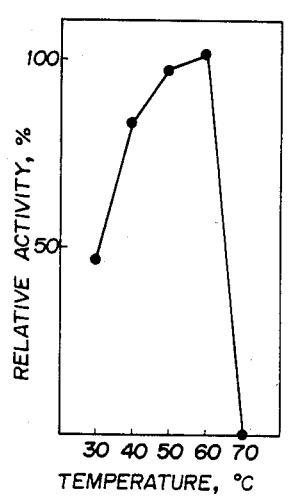
Figure 18:
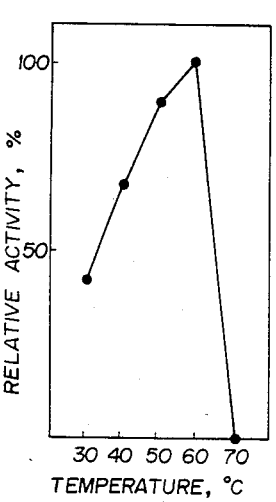
Figure 19:
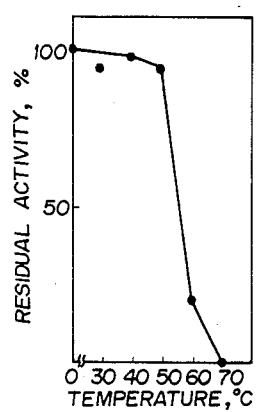
FIGS. 19 to 24 are each a graph showing the residual fibrinolytic activity of the 6 proteases, respectively, at varied temperatures after 60 minutes with a pH of 7.8.
Figure 20:
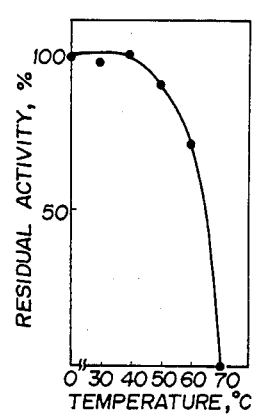
Figure 21:
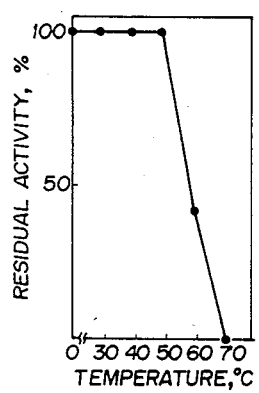
Figure 22:
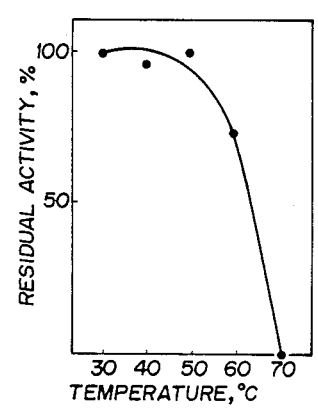
Figure 23:
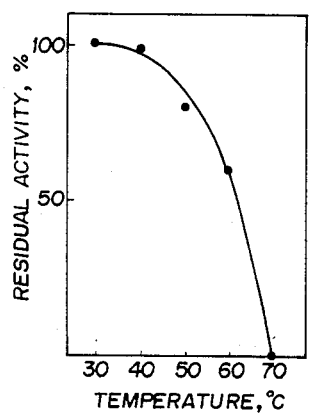
Figure 24:
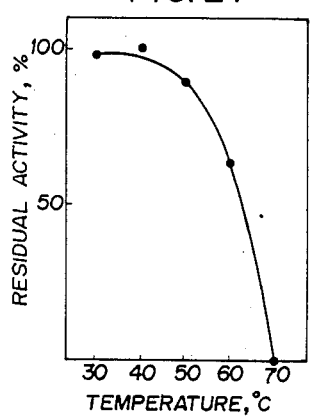
Figure 25:
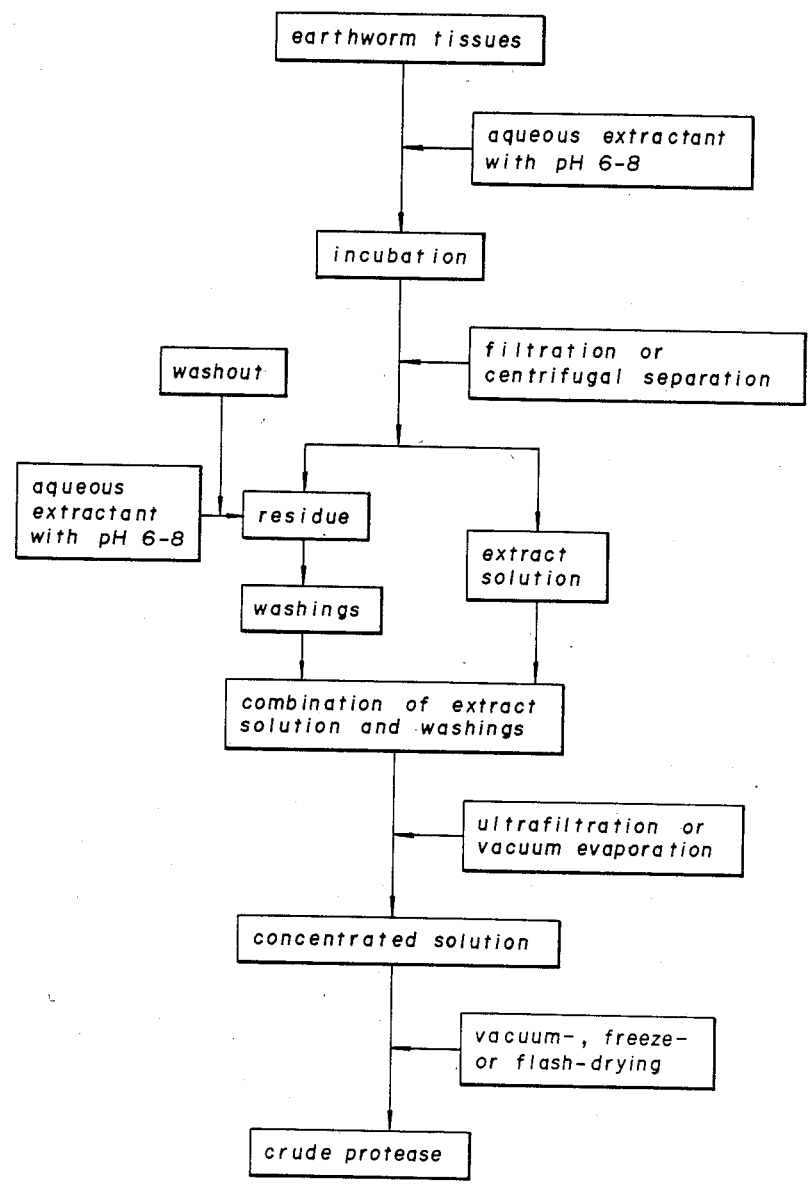
FIGS. 25 to 40 are each a flowchart of the scheme for the preparation and purification of the inventive thrombolytic agent.
Figure 26:
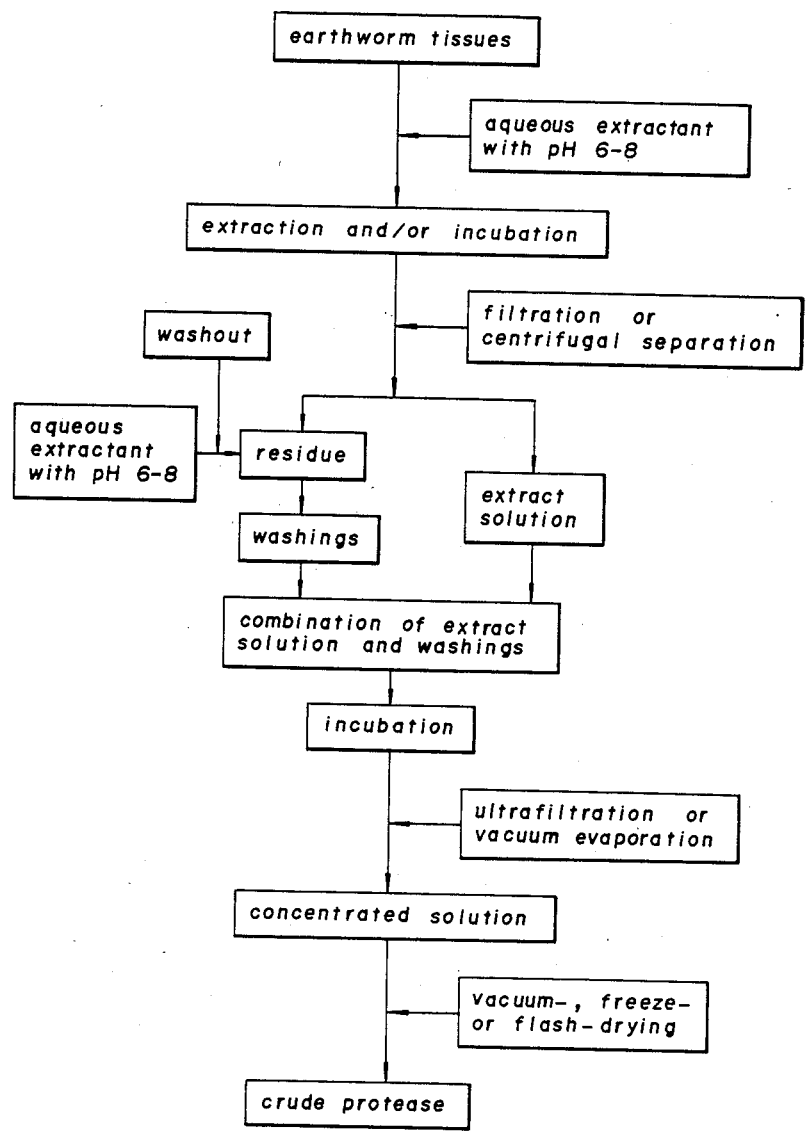
Figure 27:
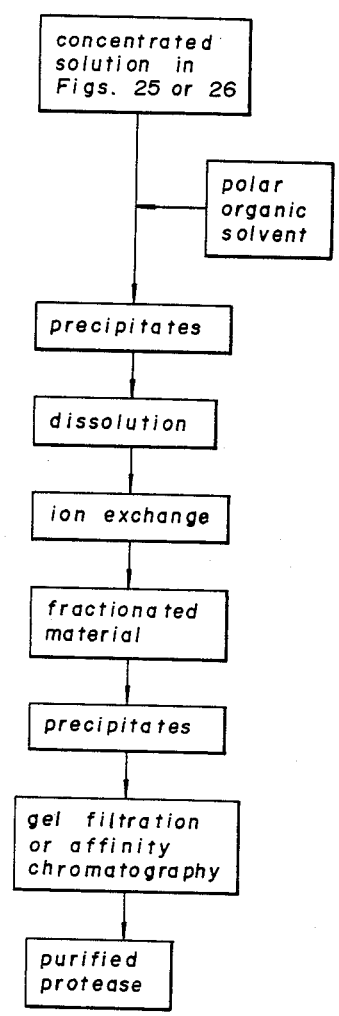
Figure 28:
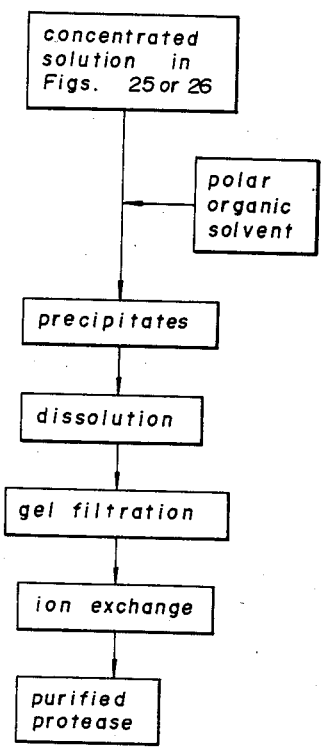
Figure 29:
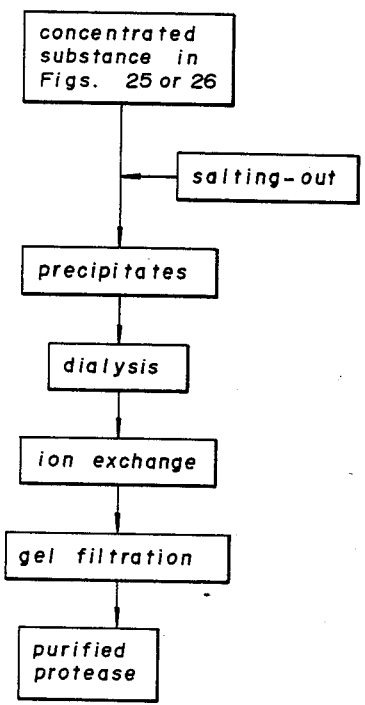
Figure 30:
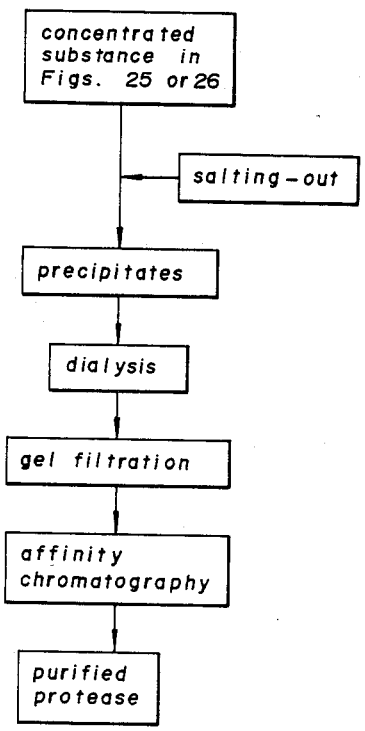
Figure 31:
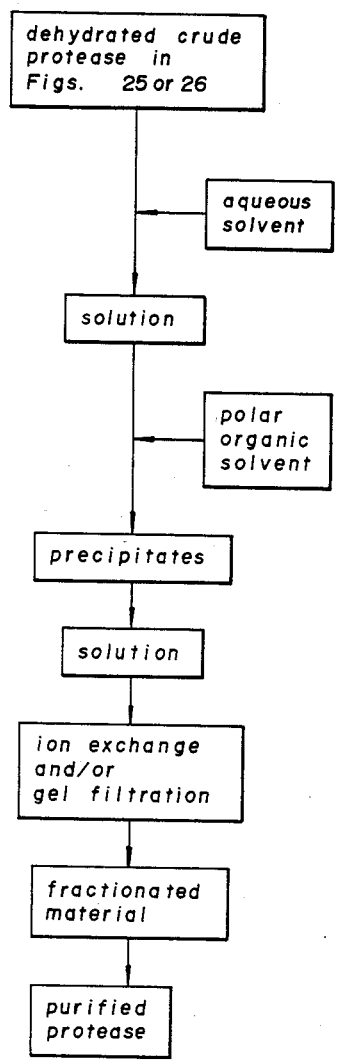
Figure 32:
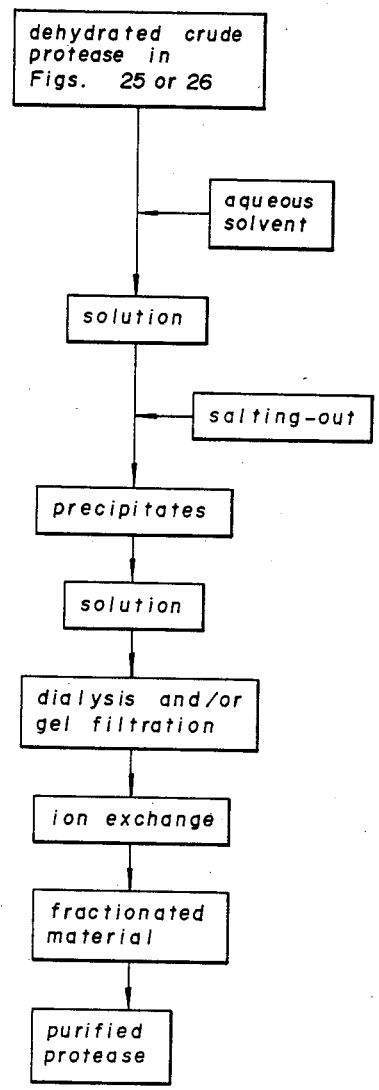
Figure 33:
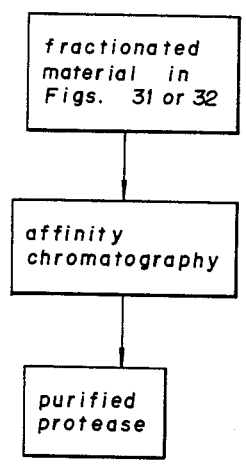
Figure 34:
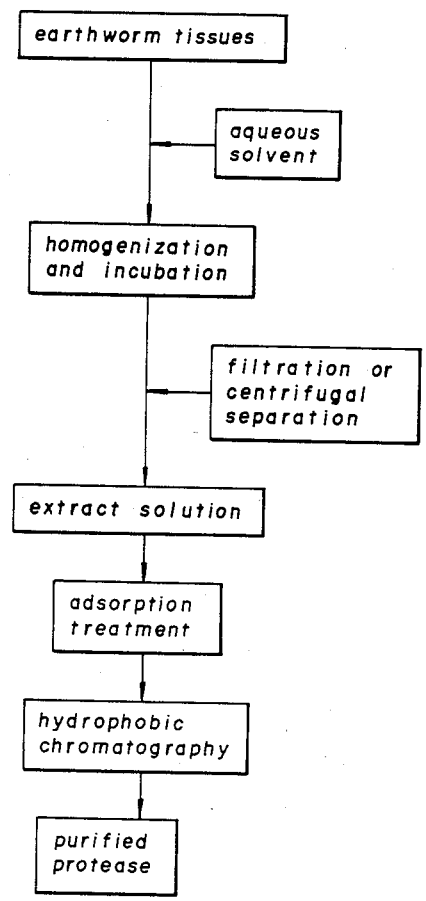
Figure 35:
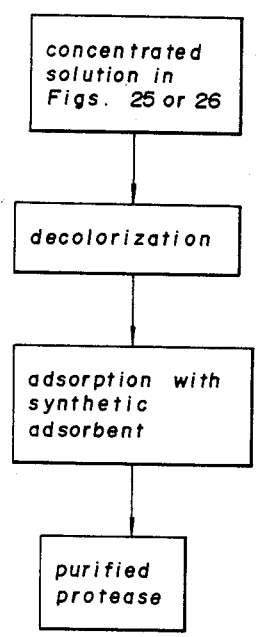
Figure 36:
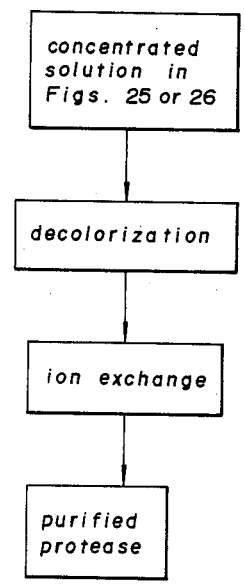
Figures 37, 38:
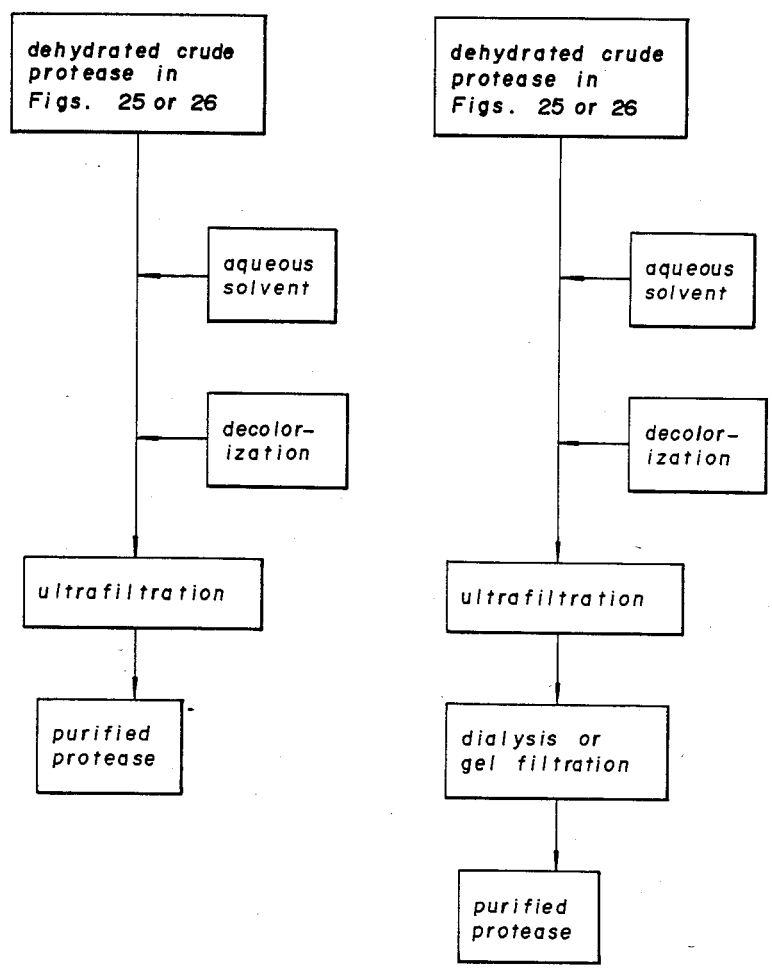
Figure 39:
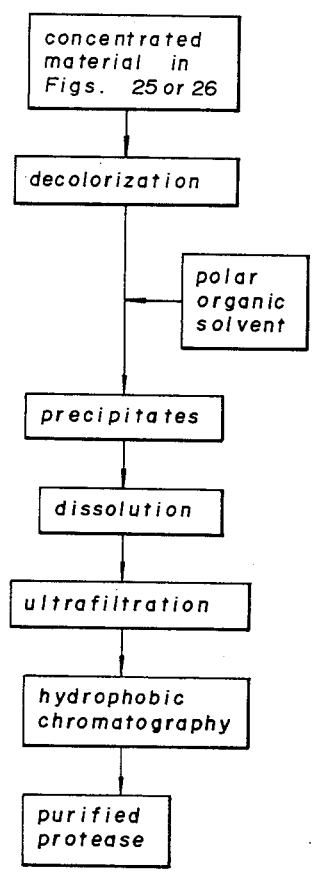
Figure 40:
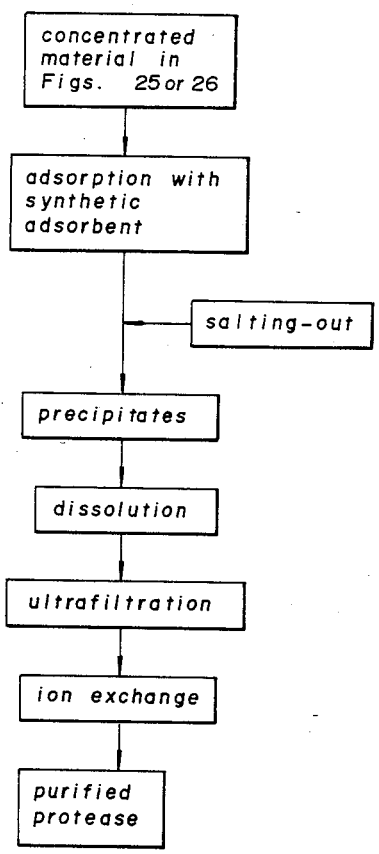

In the first place, a characterizing description is given of the proteases as the effective ingredients in the inventive thrombolytic agent. Each of the proteases is an enzyme obtained as a white amorphous powder having following physico-chemical properties.

(A) Activity and substrate specificity

The above named novel proteases have an activity for the decomposition of fibrin, an activity for the plasminogen activation, an activity for the hydrolysis of casein and several kinds of other substrates as given below. The methods for the determination of the respective activities are described later.

HM-27 has an activity for the fibrinolysis of coagulated fibrin and an activity for the plasminogen activation. It is active on casein, tosyl-L-arginine methyl ester hydrochloride (referred to as TAMe hereinafter), after), N-α-tosyl-L-lysine methyl ester hydrochloride (referred to as TLMe hereinafter), L-pyroglutamylglycyl-L-arginine-p-nitroanilide hydrochloride (usually called Testzym S-2444 chromogenic substrate available as a commercial product supplied by Daiichi Kagaku Yakuhin Kogyo Co. and referred to as S-2444 hereinafter) and H-D-valyl-L-leucyl-L-lysine-p-nitroanilide dihydrochloride (usually called Testzym S-2251 chromogenic substrate available as a commercial product supplied by the same company as for S-2444 and referred to as S-2251 hereinafter). It is, however, almost inactive on N-benzoyl-L-alanine methyl ester (referred to as BAMe hereinafter) and N-benzoyl-L-tyrosine ethyl ester (referred to as BTMe hereinafter).

HM-89 has an activity for the fibrinolysis of coagulated fibrin and an activity for plasminogen activation. It is active on casein, TAMe, TLMe, S-2444 and S-2251 but almost inactive on BAMe and BTEe.

HM-45 has an activity for the fibrinolysis of coagulated fibrin and an activity for plasminogen activation. It is active on casein, TAMe and BTMe and very weakly active on S-2444 and S-2251 but almost inactive on BAMe and TLMe.

HM-54 has an activity for the fibrinolysis of coagulated fibrin and an activity for plasminogen activation. It is active on casein, TAMe and BTMe and weakly active on TLMe and S-2444 but almost inactive on BAMe and S-2251.

HM-15 has an activity for the fibrinolysis of coagulated fibrin and an activity for plasminogen activation. It is active on casein, TAMe and BTEe and weakly active on TLMe and S-2444 but almost inactive on BAMe and S-2251.

HM-64 has an activity for the fibrinolysis of coagulated fibrin and an activity for plasminogen activation. It is active on casein and somewhat less strongly active on TAMe and weakly active on TLMe and S-2444 but very weakly active on S-2251 but almost inactive on BAMe and BTEe.

As is understood from the above summary, each of these six kinds of the novel proteases has the substrate specificity different more or less from that of the others. The values of the activity of these six proteases in the enzymatic units u/mg on the various substrates above mentioned are shown in Table 1 below together with the values of the activity for the fibrinolysis of coagulated fibrin and the activity for plasminogen activation expressed in the unit of $mm^2/mg$. In the above explanation, the expressions "active", "less strongly active", "weakly active", "very weakly active" and "almost inactive" correspond to the values of activity 1 u/mg or larger, at least 0.1 but smaller than 1 u/mg, at least 0.01 but smaller than 0.1 u/mg, at least 0.001 but smaller than 0.01 u/mg and smaller than 0.001 u/mg as indicated by N.D., i.e. "not detected", in the table, respectively.

(1) Determination of the activity for the fibrinolysis of coagulated fibrin was performed by a method similar to that described by T. Astrup in Arch. Biophys., volume 40, page 346 (1952). Thus, fibrinogen was dissolved in a 0.17M borate buffer solution at a pH of 7.8 containing 0.01M sodium chloride in such an amount that the concentration of the coagulable protein in the solution was 0.15% and 10 ml of the solution were taken in a sterilized glass dish of 80 mm diameter with admixture of 0.5 ml of a thrombin solution of 20 u/ml concentration followed by standing at room temperature for 1 hour with a glass cover. This is called the standard fibrin plate.

An aqueous solution of the enzyme under testing in an appropriate concentration was prepared, for example, by dissolving the powdery enzyme in a concentration of 1 mg/ml followed by suitable dilution and 0.03 ml of the diluted solution was dropped vertically on to the center portion of the above prepared standard fibrin plate which was, after standing as such for 10 minutes with a filter paper inserted between the glass dish and the cover, kept for 18 hours in a thermostat controlled at 37° C. to effect the reaction. The fibrinolytic activity of the enzyme, i.e. the activity for the decomposition of fibrin, on the coagulated fibrin was expressed in $mm^2$ by the product of the major and minor axes in mm of the dissolved area on the standard fibrin plate as multiplied by the ratio of dilution. The final results are given in $mm^2/ml$ for the enzyme obtained as an aqueous solution and in $mm^2/mg$ for the enzyme obtained in a powdery form.

(2) The method for the determination of the activity for the plasminogen activation was as follows. Thus, an aqueous solution was prepared by mixing 10 $\mu l$ of a solution of plasminogen (a product by Sigma Co.) in a concentration of 5 $\mu/ml$, 20 $\mu l$ of the aqueous solution of the enzyme under testing and 30 $\mu l$ of a 0.17M borate buffer solution at a pH of 7.8 containing 0.01M sodium chloride and, after standing as such for 10 minutes, 0.03 ml of the solution was dropped on to a fibrin plate prepared with a plasminogen-free fibrin (a product of Miles Laboratories, Inc.) which was kept at 37° C. for 18 hours to effect the reaction. The area X in which dissolution took place was measured and expressed in $mm^2$ as a product of the major and minor axes in mm. Similar measurement was undertaken with replacement of the above mentioned plasminogen solution with the same volume of the 0.17M borate buffer solution and the dissolved area Y was measured and expressed in $mm^2$ also as a product of the major and minor axes in mm. The activity for plasminogen activation was given by X - Y.

(3) The determination of the activity for the hydrolysis of casein was performed by a method similar to that described by M. Kunitz in J. Gen. Physiol., volume 30, page 291 (1947). Thus, 1 ml of an aqueous solution prepared by 1.5% by weight of milk casein (a product by Merck Co.) in a 0.1M phosphate buffer solution at a pH of 8.0 was admixed with 1 ml of the aqueous solution of the enzyme under testing to effect the reaction at 37° C. for 30 minutes followed by interruption of the reaction by adding 2.0 ml of a 0.4M aqueous solution of trichloroacetic acid and, after 15 minutes of incubation, subjected to centrifugal separation at 4000 r.p.m. for 15 minutes to give a clear supernatant solution which was subjected to the spectrophotometric determination at a wavelength of 280 nm by use of a reference solution prepared in a similar manner to the above by successively admixing the casein solution, aqueous solution of trichloroacetic acid and aqueous solution of the enzyme under testing. The results are expressed in the Kunitz unit.

(4) The activity for the hydrolysis of TAMe was determined according to the procedure described in Methods in Enzymology, volume 19, page 41 (1970). Thus, 19.7 mg of TAMe were dissolved in 50 ml of a 0.1M tris/hydrochloric acid buffer solution having a pH of 8.0 and 3.0 ml of this solution were mixed with 0.15 ml of the aqueous solution of the enzyme under testing to effect the reaction at 25° C. for 1 minute followed by the photometric determination of the absorbance of the solution at a wavelength of 247 nm by use of a reference solution prepared in the same manner as above excepting the use of pure water in place of the enzyme solution. The amount of the enzyme capable of hydrolyzing 1$\mu$ mole of TAMe for 1 minute was taken as 1 unit of the activity.

(5) The procedure for the determination of the activity for the hydrolysis of TLMe was substantially the same as in the determination of the activity for the hydrolysis of TAMe described above excepting the use of TLMe in place of TAMe and the use of a wavelength of 250 nm instead of 247 nm for the spectrophotometry. The amount of the enzyme capable of giving an absorbance increase of 1.0 at 250 nm for 1 minute of the reaction was taken as 1 unit of the activity.

(6) The activity of the enzyme for the hydrolysis of BTEe was determined according to the procedure described in Methods in Enzymology, volume 19, page 31 (1970). Thus, 15.7 mg of BTEe were dissolved in 30 ml of methyl alcohol followed by dilution with water to give a total volume of 50 ml and further admixture of 46.7 ml of a 0.1M tris/hydrochloric acid buffer solution having a pH of 8.0. The reaction was performed by mixing 3.0 ml of the thus prepared solution of BTEe and 0.15 ml of the aqueous solution of the enzyme at 25° C. for 1 minute and the photometric absorbance of the solution was determined at a wavelength of 256 nm by use of a reference solution prepared in the same manner as above excepting the use of pure water in place of the enzyme solution. The amount of the enzyme capable of hydrolyzing 1$\mu$ mole of BTEe for 1 minute was taken as 1 unit of the activity.

(7) The procedure for the determination of the activity for the hydrolysis of BAMe was substantially the same as in the activity determination for the hydrolysis of BTEe described above excepting the use of a solution prepared by dissolving 19.7 mg of BAMe in 50 ml of the same buffer solution in place of the BTEe solution and the use of a photometric wavelength of 255 nm instead of 256 nm. The amount of the enzyme capable of giving an absorbance increase of 1.0 at 255 nm for 1 minute of the reaction was taken as 1 unit of the activity.

(8) The activity for the hydrolysis of S-2444 was determined according to the procedure described in The Journal of Biological Chemistry, volume 265, page 2005 (1980). Thus, S-2444 was dissolved in a 0.05M tris/hydrochloric acid buffer solution having a pH of 7.4 and containing 0.1M of sodium chloride in a concentration of 0.5 mM and 1 ml of this substrate solution was admixed with 10 $\mu$l of the aqueous solution of the enzyme to effect the reaction at 25° C. for 1 minute followed by the determination of the increment in the absorbance at a wavelength of 405 nm. The amount of the enzyme capable of hydrolyzing 1$\mu$ mole of S-2444 for 1 minute was taken as 1 unit of the activity.

(9) The procedure for the determination of the activity for the hydrolysis of S-2251 was substantially the same as in the case of S-2444 described above excepting the use of S-2251 in place of S-2444 and the decrease of the concentration of the substrate to 0.1 mM from 0.5 mM. The amount of the enzyme capable of hydrolyzing 1$\mu$ mole of S-2251 for 1 minute of the reaction was taken as 1 unit of the activity.

Table 1 below gives the results of the activity determination for the combinations of the 6 enzymes, i.e. HM-27, HM-89, HM-45, HM-54, HM-15 and HM-64, and the above mentioned various substrates. In the table, "N.D." means that almost no activity was detected for the combination.

TABLE 1

| Type of activity | Protease | | | | | |
|---|---|---|---|---|---|---|
| | HM-27 | HM-89 | HM-45 | HM-54 | HM-15 | HM-64 |
| Fibrinolysis of coagulated fibrin, $\times 10^3$ mm$^2$/mg | 332 | 371 | 112 | 221 | 183 | 92.5 |
| Plasminogen activation, $\times 10^3$ mm$^2$/mg | 12.8 | 14.1 | 1.7 | 3.4 | 7.6 | 3.3 |
| Hydrolysis of casein, u/mg | 1.83 | 1.92 | 4.57 | 6.05 | 3.62 | 1.97 |
| Hydrolysis of TAMe, u/mg | 151 | 50.7 | 1.18 | 7.39 | 6.60 | 0.12 |
| Hydrolysis of BAMe, u/mg | N.D. | N.D. | N.D. | N.D. | N.D. | N.D. |
| Hydrolysis of TLMe, u/mg | 61.3 | 25.6 | N.D. | 0.016 | 0.014 | 0.012 |
| Hydrolysis of BTEe, u/mg | N.D. | N.D. | 2.43 | 3.35 | 2.63 | N.D. |
| Hydrolysis of S-2444, u/mg | 103 | 226 | 0.006 | 0.028 | 0.038 | 0.054 |
| Hydrolysis of S-2251, u/mg | 27.8 | 4.57 | 0.007 | N.D. | N.D. | 0.006 |

(B) Ranges of optimum pH and pH of stability

The optimum pH of each of the proteases was determined for the fibrinolysis of coagulated fibrin by the measurements of the activity at varied values of the pH. The results in the determination of the relative activity are plotted in FIGS. 1 to 6 for HM-27, HM-89, HM-45, HM-54, HM-15 and HM-64, respectively, taking the highest value as 100%. The white and black circles on the curves in these figures represent the data obtained by use of a phosphate buffer solution and a tris/glycine buffer solution, respectively. The values of the optimum pH are tabulated in Table 2.

Futher, the range of pH of stability was determined for each of the proteases by measuring the residual activity of the protease after keeping at 37° C. for 60 minutes under varied values of the pH. The results in the determination of the relative residual activity for the above-mentioned 6 proteases are plotted in FIGS. 7 to 12, respectively, taking the highest value as 100%. The white circles, black circles and triangles on the curves in these figures represent the data obtained by use of an acetate buffer solution, a phosphate buffer solution and a tris/glycine buffer solution, respectively. The ranges of the pH of stability are tabulated in Table 2.

(C) Range of operable temperature

The relative activity of each of the proteases for the fibrinolysis of coagulated fibrin was determined at varied temperatures by the reaction for 2 hours with a pH of 7.8. The results of the relative activity for the above mentioned 6 proteases are plotted in FIGS. 13 to 18, respectively, taking the highest value as 100%. The ranges of the operable temperature as well as the optimum temperatures are tabulated in Table 2.

(D) Deactivation Temperature

Each of the 6 proteases was kept at varied temperatures of 30 to 70° C. for 60 minutes with a pH of 7.8 and the residual activity for the fibrinolysis of coagulated fibrin was determined. The results are plotted in FIGS. 19 to 24 for the above named 6 proteases, respectively, taking the initial activity as 100%. As is seen from these figures, each of the proteases was completely deactivated by keeping at 70° C. for 60 minutes.

(E) Molecular weight

The molecular weight of each of the 6 proteases was determined by the method of electrophoresis with SDS polyacrylamide gel with bovine serum albumin (molecular weight 67,000), ovalbumin (molecular weight 43,000) and chymotrypsinogen A (molecular weight 25,000) as the standards for the molecular weight determination. The results are tabulated in Table 2 each with a probable error of ±2,000.

(F) Ultraviolet absorption spectrum

Each of the 6 proteases has an absorption maximum at a wavelength of about 280 nm and an absorption minimum at about 250 nm.

(G) Isoelectric point

Table 2 also gives the values of pH at the isoelectric point of the 6 proteases. The probable error in each of the values is ±0.1.

TABLE 2

| | Protease | | | | | |
|---|---|---|---|---|---|---|
| | HM-27 | HM-89 | HM-45 | HM-54 | HM-15 | HM-64 |
| Optimum pH | ca. 8 | ca. 8 | 8–10 | 8–10 | 8–10 | 7–8 |
| pH of stability | 5–12 | 4–12 | 4–12 | 4–12 | 4–12 | 5–12 |
| Operable temperature, °C. | 30–60 | 30–60 | 30–60 | 30–60 | 30–60 | 30–60 |
| Optimum temperature, °C. | ca. 50 | 50–60 | 50–60 | 50–60 | 50–60 | 50–60 |
| Molecular weight | 32,400 | 32,800 | 24,500 | 27,500 | 27,000 | 27,800 |
| pH at isoelectric point | 3.6 | 3.5 | 4.1 | 4.0 | 3.9 | 3.8 |

(H) Influences of Inhibitors

The influences of various enzyme inhibitors on the activity of the 6 proteases were examined in the following manner. Thus, 80 μl of an aqueous solution of one of the proteases in a concentration of 2.5 μg/ml for HM-27 and HM-89, 25 μg/ml for HM-45 and HM-64 and 12.5 μg/ml for HM-54 and HM-15 were admixed with 20 μl of an aqueous solution of an inhibitor in a concentration of 4 mg/ml and, after standing for 10 minutes at 37° C., the activity of the protease solution for the fibrinolysis of coagulated fibrin was determined by taking 30 ml of the solution. The results are summarized in Table 3 taking the uninhibited activity as 100%. The inhibitors tested were: lima bean trypsin inhibitor as a protease inhibitor; difluorophosphate as a serine reagent; N-ethyl maleimide as an SH reagent; soybean trypsin inhibitor; disodium ethylenediamine tetraacetate (referred to as EDTA in Table 3) as a chelating agent for divalent cations; egg white trypsin inhibitor; pepstatin; Antipain; chymostatin; trans-4-(aminomethyl)cyclohexane carboxylic acid (referred to as t-AMCHA in Table 3); Leupeptin; Trasylol (a product name by Baeyer Co.); and ε-aminocaproic acid. As is seen from Table 3, the inhibiting effects of these inhibitors widely differ among the 6 proteases excepting the lima bean tryprin inhibitor and difluorophosphate by which all of the proteases were completely inhibited.

TABLE 3

| | Protease | | | | | |
|---|---|---|---|---|---|---|
| Inhibitor | HM-27 | HM-89 | HM-45 | HM-54 | HM-15 | HM-64 |
| Lima bean trypsin inhibitor | 0% | 0% | 0% | 0% | 0% | 0% |
| Difluorophosphate | 0 | 0 | 0 | 0 | 0 | 0 |
| N—Ethyl maleimide | 100 | 100 | 74 | 0 | 0 | 0 |
| Soybean trypsin inhibitor | 0 | 0 | 0 | 18 | 89 | 0 |
| EDTA | 100 | 100 | 100 | 100 | 73 | 100 |
| Egg white trypsin inhibitor | 47 | 60 | 57 | 71 | 48 | 37 |
| Pepstatin | 88 | 90 | 91 | 100 | 80 | 25 |
| Antipain | 0 | 0 | 0 | 100 | 93 | 83 |
| Chymostatin | 75 | 76 | 0 | 87 | 77 | 15 |
| t-AMCHA | 49 | 47 | 30 | 83 | 66 | 23 |
| Leupeptin | 0 | 0 | 0 | 36 | 28 | 100 |
| Trasylol | 0 | 0 | 0 | 100 | 100 | 30 |
| ε-Aminocaproic acid | 68 | 70 | 38 | 100 | 80 | 50 |

(I) Composition of Amino Acids

The amino acid analysis of each of the 6 proteases was conducted in an automatic amino acid analyzer after hydrolyzing 0.2 mg of the protease diluted to a volume of 0.5 ml admixed with norleucine as an internal standard and acidified with 6N hydrochloric acid followed by heating at 110° C. for 24 hours. The results are summarized in Table 4 in % by moles.

(J) Elementary Analysis

The results of the elementary analysis of each of the 6 proteases are shown in Table 4 for carbon, hydrogen, nitrogen and sulfur.

TABLE 4

|  |  | Protease | | | | | |
| --- | --- | --- | --- | --- | --- | --- | --- |
|  |  | HM-27 | HM-89 | HM-45 | HM-54 | HM-15 | HM-64 |
| Composition of amino acids, % by moles | Aspartic acid | 15.25 | 14.99 | 12.26 | 15.65 | 16.06 | 14.81 |
|  | Threonine | 6.09 | 6.24 | 12.22 | 8.25 | 8.46 | 8.40 |
|  | Serine | 10.08 | 10.39 | 9.38 | 11.30 | 10.85 | 12.05 |
|  | Glutamic acid | 7.04 | 7.63 | 3.97 | 6.05 | 6.13 | 6.04 |
|  | Proline | 0.55 | 0.57 | 0.40 | 0.37 | 0.41 | 0.44 |
|  | Glycine | 12.66 | 12.89 | 13.48 | 15.39 | 15.41 | 14.48 |
|  | Alanine | 6.90 | 6.57 | 12.95 | 9.49 | 9.45 | 10.27 |
|  | Cysteine | 1.36 | 1.40 | 1.44 | 1.09 | 1.67 | 0.80 |
|  | Valine | 10.33 | 10.67 | 7.03 | 5.46 | 5.51 | 7.77 |
|  | Methionine | 1.36 | 1.34 | 0.55 | 0.97 | 0.82 | 0.98 |
|  | Isoleucine | 7.89 | 7.62 | 5.83 | 6.54 | 6.64 | 5.96 |
|  | Leucine | 3.73 | 3.41 | 7.47 | 7.95 | 8.01 | 7.46 |
|  | Tyrosine | 4.63 | 4.83 | 3.91 | 3.69 | 3.79 | 3.24 |
|  | Phenylalanine | 3.09 | 2.67 | 2.00 | 1.11 | 1.11 | 0.58 |
|  | Tryptophan | 0.83 | 1.09 | 0.64 | 0.98 | N.D. | 1.63 |
|  | Lysine | 1.65 | 1.67 | 0.04 | 0.50 | 0.53 | 0.45 |
|  | Histidine | 2.37 | 2.12 | 2.45 | 2.75 | 2.73 | 2.30 |
|  | Arginine | 4.19 | 3.90 | 3.98 | 2.46 | 2.42 | 2.34 |
| Elementary analysis, % by weight | C | 48.61 | 47.53 | 48.30 | 48.93 | 46.15 | 48.23 |
|  | H | 6.58 | 6.55 | 6.84 | 6.65 | 6.64 | 6.53 |
|  | N | 14.75 | 14.59 | 15.88 | 15.95 | 16.02 | 15.93 |
|  | S | 2.03 | 2.06 | 2.07 | 1.34 | 2.05 | 1.43 |

Following is a description of the procedure for the preparation of the 6 novel proteases as the effective ingredients of the inventive thrombolytic agent.

In the first place, a crude mixture of the proteases is obtained by extracting earthworm tissues with an aqueous extractant in which the earthworm tissues are finely dispersed and kept for a suitable length of time at a suitable temperature followed by the removal of the insoluble matter and, after keeping the aqueous extract solution for a suitable length of time at a suitable temperature according to need, concentration or dehydration of the extract solution. The starting material, i.e. earthworm tissues, may be finely ground live earthworms as well as fresh earthworm bodies without entrails, and the entrails, and powders of earthworms obtained by vacuum drying or freeze drying with or without defatting. The most preferable starting material is a freeze-dried powder of earthworms with or without defatting.

The aqueous extractant should have a pH of 5 to 10 or, preferably, 6 to 8. Suitable aqueous extractant is exemplified by water, physiological saline solutions, buffer solutions and prepared salt solutions either alone or as a mixture of two kinds or more. The aqueous extractant may be admixed with a small volume of a water-miscible polar organic solvent such as methyl alcohol, ethyl alcohol, propyl alcohol, acetone, diethyl ether, dioxane and the like according to need. The most preferable aqueous extractants are physiological saline solutions and buffer solutions, which latter may be a phosphate buffer solution, acetate buffer solution, borate buffer solution, citrate buffer solution, tris/hydrochloric acid buffer solution and the like having a pH of 5 to 10 or, preferably, 6 to 8 used either alone or as a mixture of two kinds or more. The above mentioned prepared salt solution implies a dilute aqueous solution prepared by mixing aqueous solutions of a water-soluble inorganic or organic acid, e.g. hydrochloric, sulfuric, phosphoric, acetic, lactic, citric and succinic acids, and an alkali including hydroxides and carbonates of an alkali metal, e.g. sodium and potassium, and ammonia water to have a pH of 5 to 10 or, preferably, 6 to 8.

The above mentioned suitable time implies a length of time up to 500 days, preferably, in the range from 30 minutes to about 30 days and the above mentioned suitable temperature implies a temperature not higher than 60° C., preferably, in the range from 5° C. to 40° C. The aqueous extractant should be added to the starting material in an amount of 1 to 100 times by weight or, preferably, 5 to 30 times by weight calculated on the base of the dry material.

The extraction of the earthworm tissues with an aqueous extractant is performed preferably by first preparing a homogenate of the constituents of the earthworm cells using a suitable instrument such as a homogenizer, blender, ultrasonic disintegrator, pressurizing cell destroyer, grinder or the like conventionally used for the cell destruction of living body tissues and incubating the homogenate before undertaking the conventional extracting means such as agitation, shaking and countercurrent flow of the extractant through a bed of the starting material. When the extraction with the aqueous extractant has come to the end, the mixture is filtrated or centrifugalized to remove the insoluble matter and the clear extract solution is, after standing for a suitable length of time at a suitable temperature if necessary, concentrated by a known method such as vacuum evaporation, heating and ultrafiltration or dehydrated by vacuum drying or freeze drying to give a crude product of the protease mixture. It is preferable to add an antiseptic agent to the extraction mixture or the extract solution under incubation in order to prevent denaturation of the effective ingredients. The addition of a small volume of a polar organic solvent as mentioned above is effective also in this respect in addition to the effect of increasing the efficiency of extraction.

The above obtained crude product of the protease mixture can be purified by subjecting the concentrated extract solution or a dehydrated material thereof dissolved in a small volume of an aqueous solvent to a known procedure for the purification of proteases. The preferable method applicable in this case is as follows. That is, the concentrated extract solution obtained in the above described procedure of extraction or an aqueous solution prepared by dissolving the dehydrated crude product in a small volume of an aqueous solvent is subjected to a treatment for the removal of the impurities by either one or a combination of the known methods including adsorption on an adsorbent, fractional precipitation with a polar organic solvent, salting-out, ultrafiltration, ion exchange chromatography, gel filtration, affinity chromatography, hydrophobic chromatography and the like. The adsorbent used in the above mentioned adsorption method may be an active charcoal, acid clay, activated clay, synthetic resin-based adsorbents such as, for example, Amberlite XAD and the like. The polar organic solvents used in the above mentioned fractional precipitation include methyl alcohol, ethyl alcohol, propyl alcohol, acetone, diethyl ether, dioxane and the like, of which ethyl alcohol, propyl alcohol and acetone are preferred. The salts used in the above mentioned salting-out include ammonium sulfate, sodium sulfate, magnesium sulfate, potassium phosphate, sodium chloride, potassium chloride, sodium citrate and the like, of which ammonium sulfate is preferred. Suitable ion exchangers used in the above mentioned ion exchange chromatography include those prepared on the base of a hydrophilic polysaccharide such as cellulose, dextran, agarose and the like. In particular, preferable anion exchangers include diethylaminoethyl cellulose (referred to as DEAE-cellulose hereinafter), triethylaminoethyl cellulose (referred to as TEAE-cellulcse hereinafter), aminoethyl cellulose (referred to as AE-cellulose hereinafter), reaction product of cellulose with epichlorohydrin and triethanolamine (referred to as ECTEOLA-cellulose hereinafter), quaternalized aminoethyl cellulose (referred to as QAE-cellulose), polyethyleneimine cellulose (referred to as PEI-cellulose), diethylaminoethyl cellulofine (referred to as DEAE-cellulofine), diethylaminoethyl sepharose (referred to as DEAE-sepharose hereinafter) and the like and preferable cation exchangers include carboxymethyl cellulose (referred to as CM-cellulose hereinafter), phosphocellulose (referred to as P-cellulose hereinafter), phosphomethyl cellulose (referred to as PPM-cellulose hereinafter), sulfoethyl cellulose (referred to as SE-cellulose hereinafter), sulfomethyl cellulose (referred to as SM-cellulose hereinafter), sulfopropyl cellulose (referred to as SP-cellulose) and the like. Commercially available ion exchange resins are also suitable as the ion exchanger in the ion exchange chromatography including, as given by the tradenames, weakly acidic cation exchange resins such as Amberlite IRC-50, Amberlite IRC-75, Amberlite IRC-84, Dowex CCR-2 and the like and strongly or weakly basic anion exchange resins such as Amberlite IR-4B, Amberlite IR-45, Amberlite IRA-400, Dowex 3 and the like. The gel filtration is performed by use of a carrier such as, as given by the tradenames, Sephadex, Sepharose, Biogel, Toyopearl Ultragel, Cellulofine and the like and the affinity chromatography is performed by use of an adsorbent such as agarose and cellulose having aliphatic, alicyclic or aromatic groups or amino-substituted groups thereof as the hydrophobic groups bonded thereto.

Several of the process schemes for the preparation of the crude products as well as purified products of the proteases are illustrated by the flowcharts given in FIGS. 25 to 40.

Following is a description of an actual example for the preparation of the inventive thrombolytic agent and the physicochemical properties and pharmacological activities of the newly obtained proteases F-I[2], F-II[1] and F-III[1] in order to more fully illustrate the entities and effectiveness of the novel proteases as the effective ingredients of the inventive thrombolytic agent.

Thus, a defatted and freeze-dried powder of earthworms was dispersed in 10 times by weight of a 50mM phosphate buffer solution having a pH of 7.0 and the mixture was incubated at 37° C. for 200 hours to extract the proteases followed by the removal of the insoluble matter by filtration and concentration of the extract solution by ultrafiltration. The concentrated solution was subjected to fractionation by the addition of ethyl alcohol and the precipitates were again dissolved in water and treated by use of DEAE-cellulose to give three fibrinolytically active fractions F-I, F-II and F-III. Each of the fractions F-I and F-II was subjected to salting-out by use of ammonium sulfate followed by the treatment with Sephadex G-75 and the fraction having activity was freeze-dried. The fraction F-III was desalted and freeze-dried as such to give a purified product.

Following description illustrates the physicochemical properties common to these proteases F-I[2], F-II[1] and F-III[1] and the activities thereof.

(1) Activity: fibrin is solubilized.

(2) Substrate specificity: fibrin is readily decomposed.

(3) Optimum pH and pH of stability: optimum pH is at around 8 to 10 and the pH of stability is in the range of about 5 to 10.

(4) Activity determination: 10 ml of a solution prepared by dissolving fibrinogen in a 0.17M borate buffer solution having a pH of 7.8 and containing 0.01 M of sodium chloride in such an amount that the concentration of the coagulable protein therein was 0.15% was taken in a sterilized glass dish of 80 mm diameter and admixed with 0.5 ml of a 20 u/ml solution of thrombin followed by standing as such at room temperature for 1 hour with a glass cover put thereon. This is called the standard fibrin plate. A 0.03 ml portion of the solution under testing was dropped vertically on to this fibrin plate and, after standing as such for 10 minutes with a filter paper inserted between the glass dish and the cover, the glass dish was placed in a thermostat controlled at 37° C. where it was kept for 18 hours to effect the reaction. The fibrinolytic activity was expressed by the product in mm$^2$ of the lengths in mm of the major and minor axes of the dissolved area formed on the fibrin plate.

(5) Stability: at least 92% of the residual activity was obtained in each of the aqueous solutions containing the protease F-I[2], F-II[1] or F-III[1] having a pH of 7.5 or 9.0 after 30 minutes at 50° C.

(6) Inhibitors: the fibrinolytic activity of proteases F-I[2], F-II[1] and F-III[1] was subject to inhibition by Trasylol (a tradename by Baeyer Co.), Transamine (a tradename by Daiichi Seiyaku Co.), soybean trypsin inhibitor (a product by Miles Lab., Inc.) and blood serum. (7) Fibrinolytic activity: the proteases F-I[2], F-II[1] and F-III[1] have an activity of plasminogen activation whereby fibrin is solubilized indirectly and also solubilize fibrin by the direct action thereon.

Following is a further detailed description of the procedure for the preparation of the proteases F-I[2], F-II[1] and F-III[1], in which the yield of the respective fractions and the fibrinolytic activity thereof are given.

Freeze-dried earthworms were defatted with acetone and 1 kg of the thus defatted and dried powder was dispersed in 10 liters of a 50 mM phosphate buffer solution having a pH of 7.0. After 100 hours of agitation at 37° C., the dispersion was filtered and the washings of the residue with 3 liters of the same buffer solution were combined with the filtrate solution to give a total volume of 12.8 liters. This solution had a fibrinolytic activity of 490 mm$^2$/ml as diluted 10 times. The liquid volume of this solution was reduced to 1.75 liters by ultrafiltration to give a concentrated solution having a fibrinolytic activity of 55 mm$^2$/ml as diluted 60 times. This concentrated solution was subjected to fractional precipitation by first adding 1.75 liters of ethyl alcohol thereto followed by filtration and then by adding 7.0 liters of ethyl alcohol to the filtrate obtained in the above mentioned filtration. The precipitates obtained in this two-step precipitation were collected and dissolved in 1.1 liters of the same phosphate buffer solution to give a solution having a fibrinolytic activity of 694 mm$^2$/ml as diluted 60 times. This solution was then treated with DEAE-Sepharose (a product by Pharmacia Co.) and fractionated into three fibrinolytically active fractions F-I, F-II and F-III. Each of the fractions F-I and F-II was subjected to salting-out by 60% saturation with ammonium sulfate and further treated with Sephadex G-75 followed by freeze-drying to give a powdery product. The yield of the products, i.e. F-I$^2$ from F-I and F-II$^1$ from F-II, was 625 mg and 665 mg, respectively, and the fibrinolytic activity thereof was 12,300 mm$^2$/mg and 10,700 mm$^2$/mg, respectively. The fraction F-III was desalted and concentrated as such followed by freeze-drying to give 1200 mg of a powdery product called F-III$^1$ having a fibrinolytic activity of 11,500 mm$^2$/mg.

The protease F-I$^2$ obtained in the above described procedure can further be fractionated and purified by the purification treatment by use of, for example, DEAE-cellulofine or Toyopearl or a combination of the treatments by use of them into single component products of novel proteases HM-45, HM-54 and HM-15 or a protease mixture F-I$^1$ which is a mixture of HM-54 and HM-15. Similarly, treatment or combination of treatments of the protease F-II$^1$ by use of, for example, Toyopearl, Hexylsepharose or DEAE-cellulofine can give a purified single component product of novel protease HM-64. Further similarly, purification of the protease F-III$^1$ by the treatment or combination of treatments with ETI (egg white trypsin inhibitor)-sepharose, DEAE-cellulofine or Toyopearl gives purified single component products of novel proteases HM-27 and HM-89. That is, the proteases F-III$^1$, F-I$^1$, F-I$^2$ and F-II$^1$ are each not a single component product but a semi-purified mixture of proteases of which the content of the proteases is at least 5% or, in most cases, at least 50%.

An alternative procedure for the preparation of these proteases is as follows. Thus, 300 g of a freezedried powder of earthworms were dispersed and homogenized in 3 liters of a physiological saline solution and the homogenate was incubated at 37° C. for 20 days to extract the effective ingredients followed by filtration thereof and freeze-drying of the filtrate solution to give a powdery product exhibiting the same properties as described above.

Figure 41:
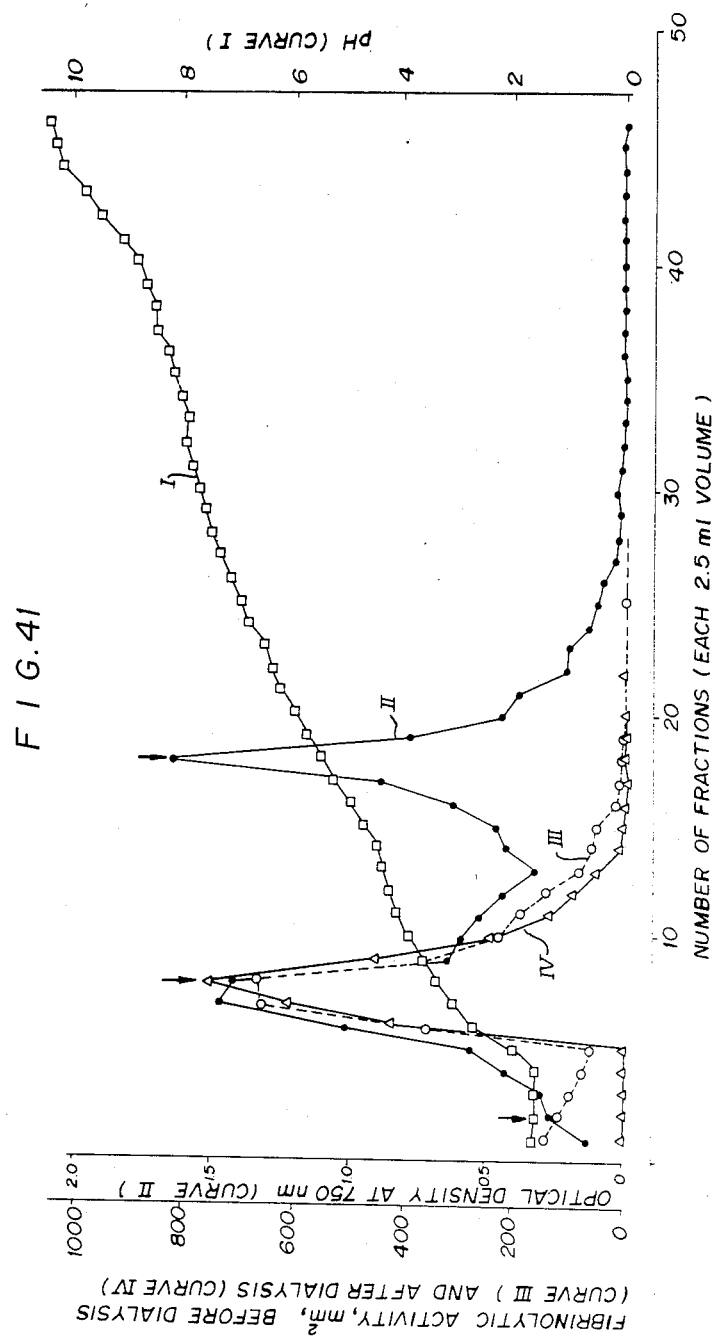
FIG. 41 is a graph of the pH gradient curve, the results of the spectrophotometric determination and the fibrinolytic activity for the fractions obtained by isoelectric focusing of an earthworm extract.

FIG. 41 illustrates the pH gradient curve of this extract solution, i.e. the filtrate, as determined by the isoelectric focusing shown by the curve plotted with the white squares and the results of the spectrophotometric determination at a wavelength of 750 nm by use of a copper-Folin reagent for the fractions each in a volume of 2.5 ml as shown by the curve plotted with the black circles. As is seen in these curves, it is apparent that the solution contained several proteases having isoelectric points at 1.5, 3.4 and 5.6 of pH. FIG. 41 also includes the curves for the fibrinolytic activity of the extract solution, i.e. the filtrate, as such and after dialysis as plotted with the white circles and the white triangles, respectively. As is understood from these results, the extract solution before dialysis contained a material having strong fibrinolytic activity appearing in the fraction having an isoelectric point of approximately pH 3.4 and also fibrinolytically active materials, though less active, having isoelectric points of approximately pH 1.5 and 4.0 while the material having an isoelectric point of approximately pH 5.6 had no fibrinolytic activity. The dialysis of the extract solution had an effect to remove the fibrinolytically active material at the isoelectric point of about pH 1.5 leaving the fibrinolytically active material at the isoelectric point of about 3.4. As a conclusion, the material having an isoelectric point of about pH 3.4 is fibrinolytically active while the material having an isoelectric point of about pH 5.6 has no fibrinolytic activity.

Following are the results of the pharmacological test and the effectiveness test undertaken with the above obtained proteases.

Test for acute toxicity: The test for the acute toxicity of the novel proteases was undertaken with the respective proteases obtained in the Examples described later. Four-week old male mice of the ddy lineage each having a body weight of 30±2 g. were used as the test animals in groups each composed of five. Each of the mice was administrated with a solution of the protease dissolved in a physiological saline solution orally, intraperitoneally or intravenously and observed over a period of 14 days after the administration for the appearance of the toxic symptoms and eventual death. The values of the LD$_{50}$ were calculated according to the Litchfield-Wilcoxon method described in J. Pharmac. Exp. Ther., volume 96, page 99 (1949).

When the administration of the protease was performed orally, no mice were killed in each of the groups even with a maximum technically possible dose of 5000 mg/kg and toxic symptoms in the living mice and abnormality by the dissective inspection could not be found at all. When the administration was performed intraperitoneally, some of the cases were concluded with death taking place within 90 minutes of the administration accompanied by asphyxial convulsion. Dissective inspection of the thus killed mice indicated hematic abdominal dropsy and spotwise bleeding on the peritoneal and enteric walls. On the other hand, the dissective inspection of the survivors indicated no abnormality. The intravenous administration of the protease resulted in the death of the mice in some cases accompanied by asphyxial convulsion. The dissective inspection of the thus killed mice indicated no abnormality excepting bleeding in the lungs. The dissective inspection of the survivors indicated no abnormality as in the intraperitoneal administration. Table 5 below summarizes the values of LD$_{50}$ for each of the proteases determined as above.

TABLE 5

| Protease | LD$_{50}$ by oral administration, mg/kg | LD$_{50}$ by intraperitoneal administration, mg/kg | LD$_{50}$ by intravenous administration, mg/kg |
|---|---|---|---|
| HM-27 | >5,000 | 92 | 33 |
| HM-89 | >5,000 | 70 | 38 |
| HM-45 | >5,000 | 60 | 114 |
| HM-54 | >5,000 | 68 | 135 |
| HM-15 | >5,000 | 48 | 88 |
| HM-64 | >5,000 | 20 | 27 |
| F-III[1] | >5,000 | — | — |
| F-II[1] | >5,000 | — | — |
| F-I[1] | >5,000 | — | — |
| F-I[2] | >5,000 | — | — |

Determination of the thrombolytic activity by the Chandler's loop method: the test solution and control solution were prepared by dissolving the protease and urokinase (a product by Otsuka Seiyaku Co.), respectively, in a physiological saline solution. The blood was taken from the vein of a single healthy male adult and immediately admixed with one-tenth volume of a 3.8% aqueous solution of sodium citrate. The reference solution for the blank test was the physiological saline solution.

Formation of thrombi and measurement of the dissolution thereof were performed in the following manner. Thus, 0.8 ml of the above obtained fresh blood admixed with sodium citrate and 0.1 ml of a 3% aqueous solution of calcium chloride as $CaCl_2 \cdot 2H_2O$ were introduced into a tube of polyvinyl chloride resin having an inner diameter of 3 mm and a length of 250 mm and the ends of the tube were connected to each other to form a loop which was put coaxially on a turntable inclined at an angle of 60° and rotated at 37° C. for 30 minutes at a velocity of 17 r.p.m. to form thrombi therein. Thereafter, 0.1 ml of one of the protease solutions, the urokinase solution or the reference solution was introduced into the loop which was rotated under the same conditions as above for 60 minutes. The thrombi remaining in the tube were then taken out and, after fixing with a Bouin's reagent, i.e. a solution prepared by adding 25 ml of a commercially available formalin solution and 5 ml of glacial acetic acid to 75 ml of a saturated aqueous solution of picric acid, the weight of the wet thrombi was measured. The thrombolytic activity of the proteases and urokinase was expressed by the ratio of the thus determined wet weight of the thrombi to the average wet weight, i.e. 43.3 mg, of the thrombi of about 3 mm diameter and 10 mm length obtained in the blank test by use of the physiological saline solution as the reference. The results are summarized as % thrombolysis in Table 6.

TABLE 6

| Concentration in blood, μg/ml | % Thrombolysis | | | | | | |
|---|---|---|---|---|---|---|---|
| | HM-27 | HM-89 | HM-45 | HM-54 | HM-15 | HM-64 | Urokinase* |
| 25 | — | — | — | — | — | 0.2 | — |
| 50 | — | — | — | — | — | 26.5 | 8.0 |
| 75 | — | — | — | — | — | 42.7 | — |
| 100 | — | — | — | — | — | 54.9 | 39.8 |
| 150 | — | — | — | — | — | 72.6 | 49.7 |
| 200 | 4.9 | — | — | — | — | 83.3 | 60.3 |
| 250 | — | — | — | — | — | — | 66.4 |
| 300 | 10.9 | — | — | — | — | — | — |
| 340 | — | — | 9.0 | 7.4 | 2.2 | — | — |
| 400 | 19.5 | 0.2 | 26.9 | 17.6 | 7.4 | — | — |
| 460 | — | — | 56.5 | 28.7 | 20.6 | — | — |
| 475 | — | 3.6 | — | — | — | — | — |
| 500 | 66.4 | — | — | — | — | — | — |
| 520 | — | 18.3 | 75.5 | 52.9 | 42.8 | — | — |
| 550 | 80.0 | 29.1 | — | — | — | — | — |
| 580 | — | — | 83.6 | 70.9 | 74.3 | — | — |
| 595 | — | 68.5 | — | — | — | — | — |
| 600 | 86.6 | — | — | — | — | — | — |
| 625 | — | 76.0 | — | — | — | — | — |
| 640 | — | — | 87.0 | 85.5 | 82.5 | — | — |
| 670 | — | 81.4 | — | — | — | — | — |
| 700 | — | 85.7 | — | — | — | — | — |
| 745 | — | 87.9 | — | — | — | — | — |

*Concentration in blood is given in Iu/ml blood.

Figure 42:
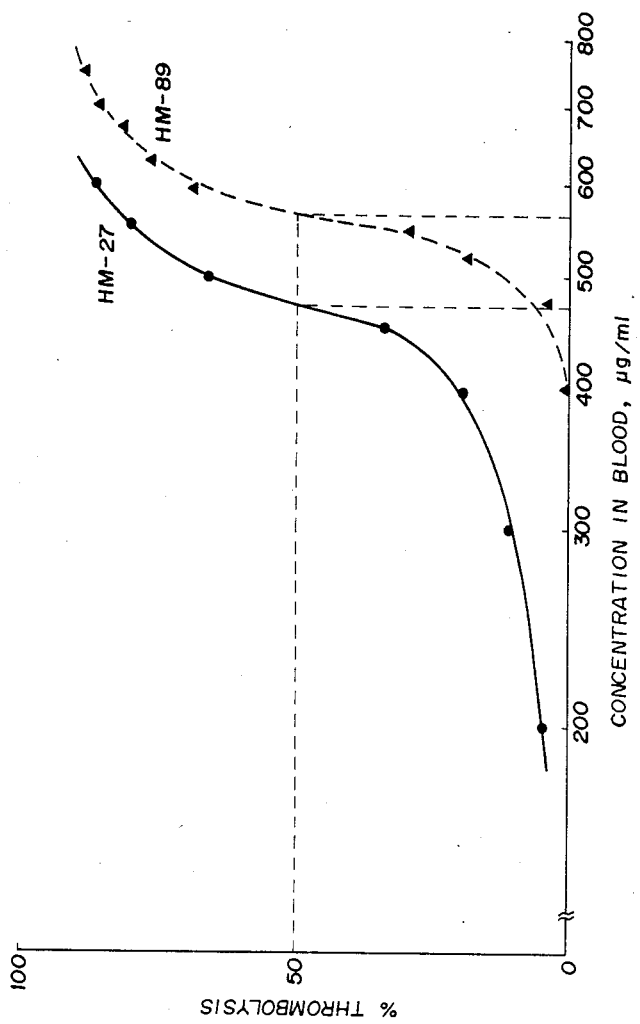
FIG. 42 is a graphical showing of the % thrombolysis as a function of the concentration of HM-27 and HM-89.

FIG. 42 is a graph showing the % thrombolysis as a function of the concentration of HM-27 and HM-89 in blood obtained by plotting the data in Table 6. Each of the curves gives the concentration of the respective protease in blood required to give 50% thrombolysis. Table 7 below gives the thus determined concentrations for 50% thrombolysis for each of the purified and semipurified proteases as well as urokinase.

TABLE 7

| Protease | Concentration in blood for 50% thrombolysis | Protease | Concentration in blood for 50% thrombolysis |
|---|---|---|---|
| HM-27 | 470 μg/ml | F-III[1] | 3600 μg/ml |
| HM-89 | 560 μg/ml | F-I[1] | 2300 μg/ml |
| HM-45 | 440 μg/ml | F-I[2] | 2200 μg/ml |
| HM-54 | 515 μg/ml | F-II[1] | 340 μg/ml |
| HM-15 | 530 μg/ml | (Urokinase) | 130 Iu/ml |
| HM-64 | 86 μg/ml | | |

The above described Chandler's loop method for the determination of the thrombolytic activity is, although it is an in vitro method, widely accepted as a simple testing method capable of giving results closely simulating the in vivo testing (see J. Exp. Physiol., XLIV (4), pages 377–384 (1959)) and the results obtained in this test well represent the thrombolytic performance of the proteases according to the invention.

Figure 43:
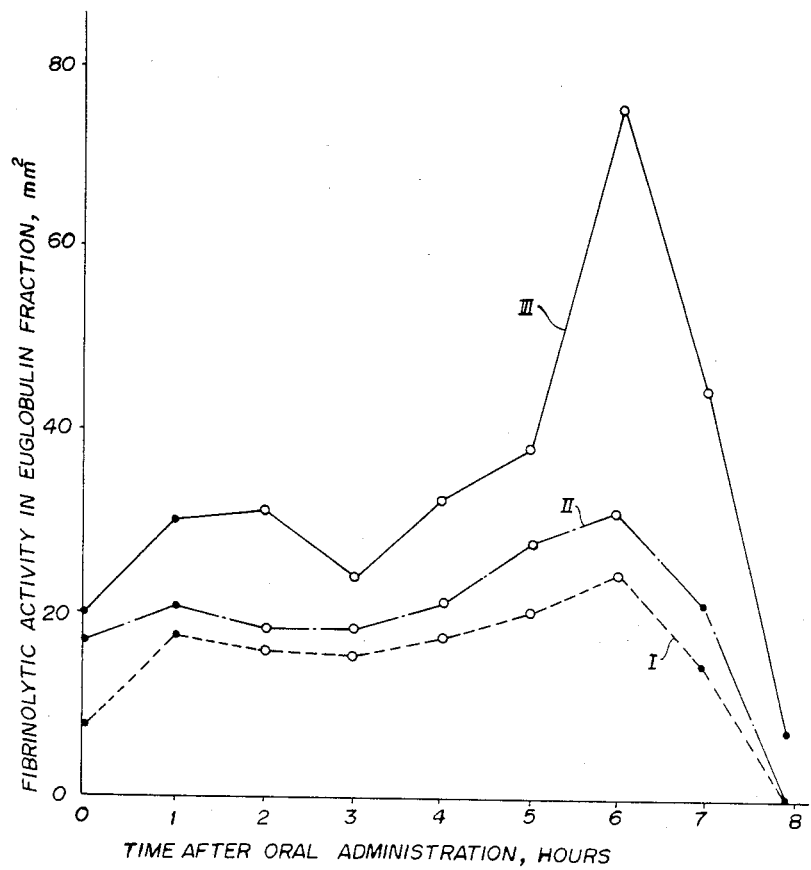
FIG. 43 is a graph showing the fibrinolytic activity of the peripheral blood of three patients orally administrated with the inventive protease F-III[1] in the lapse of time.

In vivo activity test of the proteases according to the invention: in the use of the proteases according to the present invention as a therapeutic medicament for human patients by oral administration, crude or partially purified products at any intermediate stages of purification in the above described purification procedure may be used although, needless to say, the highly purified final products are the most preferable form and excellent thrombolytic effectiveness can be obtained by oral administration. Thus, three male human patients of 60, 73 and 59 years old suffering arteriosclerosis were each orally administered with 600 mg of the freeze-fried product of F-III[1] obtained in the Example given later and the peripheral blood of each patinet was taken periodically at intervals, for which the fibrinolytic activity in mm[2] was examined by the euglobulin fractionation to give the results shown in FIG. 43, in which white circles indicate complete solubilization and the black circles indicate incomplete solubilization and Curves I, II and III correspond to the patients of 60, 73 and 59 years old, respectively. As is clear from these results, the fibrinolytic activity in the peripheral blood began to increase at about 2 hours after administration of the test medicine and reached a maximum value at 4 to 6 hours after administration.

The novel proteases according to the present invention are novel harmless enzymes first obtained by the inventors from earthworms and expectedly have following clinical effects by virtue of the excellent fibrinolytic and thrombolytic activities.

Generally, the fibrin converted from fibrinogen by enzymes makes one of the important factors for the appearance of thrombosis and infarction. Therefore, the novel proteases according to the present invention are expected to have preventive and therapeutic effects by the above mentioned activities for thrombosis in peripheral veins and arteries, pulmonary embolism, coronary occlusion, mycocardial infarction, cerebral infarction, retinal thrombosis, hemorrhagia corporis vitrei, hyphema and the like. Further, a synergistic effect against malignant tumors may be expected by the combined use of them with an antitumor agent and effects may be expected in the use of them as an anticoagulant in blood transfusion, for preventing embolus formation along the seam lines in vascular operation and for long-term maintenance of the performance of the vascular shunt in blood dialysis.

The medicament form of the inventive thrombolytic agent may be oral or non-oral when it is administrated to patients with a therapeutic purpose although it shoud preferably be in a form suitable for oral administration. An estimated clinical dose is preferably in the range from 0.1 $\mu$g to 1000 mg or, preferably, from 10 $\mu$g to 300 mg per day per patient. The proteases according to the invention are of course effective also in the veterinary medicine as a thrombolytic agent for mammalian animals other than human with a preferable daily dose of 0.1 $\mu$g to 100 mg per kg of the body weight.

The medicament forms of the proteases according to the present invention may be prepared by various procedures, for example, by the method in which an aqueous solution of the proteases is, with or without admixture of additives, freeze-dried into a powdery form, or by the method in which a freeze-dried powder of the proteases is admixed with additives according to need. The additives to be admixed with the proteases include, according to the particular purpose of administration, stabilizers such as mannit, dextrin, albumin, gelatin, hydroxyethylated starch, glycine, lysine, arginine, sucrose, polyvinyl pyrrolidone, sodium hydrogensulfite and the like, pH controlling agent such as sodium phosphate, sodium citrate, sodium hydroxide and the like, isotonic agents such as sodium chloride, mannit, sorbit, glucose and the like and plasmin-inhibitor activating agents or absorption accelerators such as sulfate esters of sugars such as dextran and sucrose as well as sodium salts thereof. It is preferable that the protease-containing thrombolytic composition according to the invention is formulated into a medicament form with admixture of at least one kind of the above named additives. The medicament forms of the inventive thrombolytic agent suitable for oral administration include conventional tablets, beads, powders, granules, sugar-coated tablets, film-coated tablets, troches, buccal tablets and enteric or non-enteric capsules as well as the medicament form in which the effective ingredients are contained in the interstices of the known liposomes prepared from phospholipids.

Any lipid may be used for the preparation of the above mentioned liposomes in a medicament form of the inventive thrombolytic agent provided that it is intoxic or physiologically acceptable and metabolizable. Typical usable lipids are phospholipids as exemplified by phosphatidyl choline, i.e. lecithin, phosphatidyl ethanolamine, phosphatidyl inositol, phosphatidyl serine, sphingomyelin and phosphatidic acid as well as cholesterol, chenodeoxycholic acid, ursodeoxycholic acid and the like. They are used either alone or as a combination of two kinds or more according to need. Further, vegetable lecithins containing a large amount of phospholipids as well as vegetable oils containing them are also suitable.

When a non-oral medicament form of the inventive thrombolytic agent is desired, in particular, for the external application, the form is preferably an ointment, lotion, liniment, suppository and the like. The base for the protease ointment of the invention may be oleic one or emulsified one exemplified by liquid paraffin, Isoper (a product by ESSO Co.), white petrolatum, silicone fluid, aliphatic higher alcohols having 16 to 20 carbon atoms per molecule, higher fatty acids having 14 to 20 carbon atoms per molecule, waxes having 16 to 30 carbon atoms per molecule, castor oil, hydrogenated vegetable oils, lanolin and derivatives thereof, squalene and squalane. Further, suitable emulsifiers and dispersing agents for the preparation of the ointment include non-ionic surface active agents of the type of an ester of a polyhydric alcohol such as monoglycerides and sorbitan esters of fatty acids having 14 to 20 carbon atoms per molecule, esters of sucrose and polyglycerin with fatty acids having 14 to 20 carbon atoms per molecule, and polyoxyethylene-based non-ionic surface active agents such as ethers of polyoxyethylene with an aliphatic alcohol having 12 to 18 carbon atoms per molecule, esters of polyoxyethylene with a fatty acid having 12 to 20 carbon atoms per molecule and derivatives of polyoxyethylene with a polyhydric alcohol, e.g. sorbitan esters of fatty acids having 14 to 20 carbon atoms per molecule and the like. The wetting agent in the ointment may be glycerin, propylene glycol, sorbit or an amino acid. It is of course optional that the thrombolytic agent of the invention in the form of an ointment may be formulated with other known additives such as stabilizers and/or anti-oxidants with no toxicity.

Suitable forms of the lotion as a medicament form of the inventive thrombolytic agent include shake mixtures, emulsions and solutions. The shake mixture-type lotions may be prepared by use of a suspending agent such as sodium alginate, tragacanth, methyl cellulose, sodium carboxymethyl cellulose, polyethylene glycol, propylene glycol monostearate and the like either alone or as a combination of two kinds or more. The emulsion-type lotions are prepared by use of an emulsifier which is preferably a non-ionic surface active agent such as Polyoxy-40 stearate, sorbitan monostearate, sodium laurylsulfate and those sold under the tradenames of Span 20 and Tween 20. The lotion-type medicament form of the inventive thrombolytic agent may of course be formulated with a known and safe anti-septic agent such as benzyl benzoate, methyl 4-hydroxybenzoate, propyl 4-hydroxybenzoate and the like.

The liniments as the medicament form of the inventive thrombolytic agent are prepared with a base such as olive oil, sesame oil, almond oil, cottonseed oil and the like vegetable oils.

The suppository forms of the inventive thrombolytic agent are prepared by use of cacao butter, Witepsol, Sabanal, polypropylene glycol, glycerogelatin or gelatin capsules.

Following are several examples of the formulation of the medicament forms containing the inventive thrombolytic agent and description of the preparation of the effective ingredients by the extraction from earthworm tissues.

Preparation 1 (Tablets)

The powdery components shown by the formulation below were uniformly blended and the mixture was tabletted into tablets each weighing 150 mg by use of a tabletting machine.

| Protease F-III-1-HM-27 | 0.1 mg |
|---|---|
| Crystalline cellulose | 44.5 |
| Lactose | 73.4 |
| Corn starch | 31.0 |
| Magnesium stearate | 1.0 |
| Total | 150 mg |

Preparation 2 (Tablets)

The powdery components shown by the formulation below were uniformly blended and the mixture was tabletted into tablets each weighing 100 mg by use of a tabletting machine.

| Protease F-I-1-HM-54 | 0.1 mg |
|---|---|
| Crystalline cellulose | 85.4 |
| Lactose | 10.0 |
| Calcium carboxymethyl cellulose | 2.0 |
| Magnesium stearate | 1.0 |
| Stearic acid | 1.5 |
| Total | 100 mg |

Preparation 3 (Beads)

The powdery components shown by the formulation below were uniformly blended and the mixture was shaped into beads by use of an extruder machine.

| Protease F-III-2-HM-89 | 0.1 mg |
|---|---|
| Crystalline cellulose | 85.4 |
| Mannitol | 10.0 |
| Calcium carboxymethyl cellulose | 2.0 |
| Magnesium stearate | 1.0 |
| Hardened oil | 1.5 |
| Total | 100 mg |

Preparation 4 (Beads)

The powdery components shown by the formulation below were uniformly blended and the mixture was shaped into beads by use of an extruder machine.

| Protease F-III[1] | 0.5 mg |
|---|---|
| Crystalline cellulose | 64.5 |
| Mannitol | 15.0 |
| Corn starch | 15.0 |
| Hydroxypropyl cellulose | 3.0 |
| Polyvinyl pyrrolidone | 2.0 |
| Total | 100 mg |

Preparation 5 (Beads)

Protease F-I[1], crystalline cellulose, lactose and corn starch were uniformly blended according to the formulation shown below and the mixture was shaped into beads by use of a fluidized-bed granulator under spray of a 5% aqueous solution of the hydroxypropyl cellulose shown in the formulation as a binder followed by drying.

| Protease F-I[1] | 0.5 mg |
|---|---|
| Crystalline cellulose | 60.0 |
| Lactose | 21.5 |
| Corn starch | 15.0 |
| Hydroxypropyl cellulose | 3.0 |
| Total | 100 mg |

Preparation 6 (Beads)

Protease F-I-2-HM-15, crystalline cellulose, mannitol, potato starch and polyvinyl pyrrolidone were uniformly blended according to the formulation shown below and the mixture was shaped into beads by use of a fluidized-bed granulator under spray of a 5% aqueous solution of the hydroxypropyl cellulose shown in the formulation as a binder followed by drying.

| Protease F-I-2-HM-15 | 0.2 mg |
|---|---|
| Crystalline cellulose | 47.8 |
| Mannitol | 38.0 |
| Potato starch | 10.0 |
| Polyvinyl pyrrolidone | 2.0 |
| Hydroxypropyl cellulose | 2.0 |
| Total | 100 mg |

Preparation 7 (Capsules)

Protease F-III-1-HM-27, crystalline cellulose, lactose, mannitol, corn starch and polyvinyl pyrrolidone were uniformly blended according to the formulation shown below and the mixture was shaped into beads by use of a fluidized-bed granulator under spray of a 5% aqueous solution of the hydroxypropyl cellulose shown in the formulation as a binder followed by drying. Hard capsules were prepared by encapsulating each 160 mg of the beads in a No. 3 hard capsule.

| Protease F-III-1-HM-27 | 0.1 mg |
|---|---|
| Crystalline cellulose | 46.9 |
| Lactose | 28.0 |
| Mannitol | 10.0 |
| Corn starch | 10.0 |
| Polyvinyl pyrrolidone | 2.0 |
| Hydroxypropyl cellulose | 3.0 |
| Total | 100 mg |

Preparation 8 (Capsules)

Hard capsules were prepared by encapsulating each 160 mg of the beads obtained in Preparation 6 in a No. 3 hard capsule.

Preparation 9 (Capsules)

Hard capsules were prepared by encapsulating each 200 mg of the beads obtained in Preparation 3 in a No. 2 hard capsule.

Preparation 10 (Capsules)

The powdery components shown by the formulation below were uniformly blended and enteric capsules were prepared by encapsulating each 200 mg of the powdery mixture in a No. 2 gelatin capsule followed by enteric coating.

| | |
|---|---|
| Protease F-0-HM-45 | 0.5 mg |
| Mannitol | 197.0 |
| Magnesium stearate | 2.5 |
| Total | 200 mg |

Preparation 11 (Capsules)

An aqueous solution in a volume of 300 ml was prepared by dissolving 1 g of protease F-I$^2$ and 199 g of sodium dextransulfate containing 17.0–20.0% of sulfur and having an intrinsic viscosity of 0.022–0.028 in distilled water and the solution was, after adjustment of the pH to 7.0 by adding disodium hydrogenphosphate, thoroughly freeze-dried. This freeze-dried material was pulverized and admixed with 98 g of mannitol and 2 g of magnesium stearate and each 300 mg portion of the powdery mixture was encapsulated in a No. 1 gelatin capsule to give a capsulated medicament.

Preparation 12 (Capsules)

An aqueous solution was prepared by dissolving 2 g of protease F-I-2-HM-15 and 198 g of a dextransulfate ester containing 3.0–6.0% sulfur and having an intrinsic viscosity of 0.030–0.045 in 300 ml of distilled water followed by the adjustment of the pH to 7.0 by adding a small volume of a 5% aqueous solution of sodium hydroxide and the solution was thoroughly freeze-dried. The freeze-dried material was pulverized and admixed with 49 g of mannitol, 49 g of albumin and 2 g of magnesium stearate and enteric capsules were prepared each by encapsulating 200 mg of the powdery mixture in a No. 2 gelatin capsule followed by enteric coating.

Preparation 13 (Beads)

A freeze-dried material was prepared in substantially the same manner as in Preparation 12 excepting the use of Protease F-I$^1$ instead of protease F-I-2-HM-15 and a 1 g portion of this freeze-dried material was admixed and blended uniformly with 65 g of crystalline cellulose, 15 g of mannitol, 15 g of corn starch, 3 g of hydroxypropyl methyl cellulose and 1 g of a copolymer of vinyl pyrrolidone and vinyl acetate (a product by General Aniline & Film Corp.) and the mixture was shaped by use of an extruder machine into spherical beads.

Enteric beads were prepared by providing the beads prepared as above with a coating composition comprising 74% of hydroxypropyl methyl cellulose phthalate, 11.6% of glyceryl triacetate, 11.6% of stearic acid and 2.8% of anhydrous light silicic acid as the solid constituents.

Preparation 14 (Tablets)

Tablets were prepared by use of a tabletting machine of a powdery mixture with the formulation shown below.

| | |
|---|---|
| Protease F-II-HM-64 | 0.1 mg |
| Crystalline cellulose | 85.4 |
| Mannitol | 10.0 |
| Calcium carboxymethyl cellulose | 2.0 |
| Magnesium stearate | 1.0 |
| Hardended oil | 1.5 |
| Total | 100 mg |

These tablets were further provided with enteric coating with a coating composition with the formulation shown below per tablet.

| | |
|---|---|
| Hydroxypropyl methyl cellulose phthalate | 14.8 mg |
| Dioctyl phthalate | 2.3 |
| Stearic acid | 2.3 |
| Anhydrous light silicic acid | 0.6 |
| Total | 20 mg |

Preparation 15 (Beads)

A powdery mixture of the following formulation was nucleated centrifugally or by rolling.

| | |
|---|---|
| Protease F-II$^1$ | 0.2 mg |
| Corn starch | 32.5 |
| Hydroxypropyl cellulose | 3.8 |
| Total | 36.5 mg |

The thus nucleated mixture was diluted with an excipient of the formulation below and shaped into beads by use of a conventional binder followed by coating.

| | |
|---|---|
| Granulated sugar | 32.5 mg |
| Corn starch | 58.5 |
| Hydroxypropyl cellulose | 2.5 |
| Total | 93.5 mg |

These beads were further coated with 30 mg of the enteric coating composition used in Preparation 14 to give enteric beads and medicament capsules were prepared each by encapsulating 160 mg of the enteric beads in a No. 3 gelatin capsule.

Preparation 16 (Powder)

A powdered medicament form was prepared by uniformly blending the components according to the following formulation.

| | |
|---|---|
| Protease F-I$^1$ | 0.5 mg |
| Mannitol | 49.5 |
| Lactose | 50.0 |
| Total | 100 mg |

Preparation 17 (Sugar-coated tablets)

A powdery mixture prepared by blending the components according to the same formulation as in Preparation 14 excepting the replacement of protease F-II-HM-64 with the same amount of protease F-I-1-HM-54 was shaped into base tablets by use of a tabletting machine. These base tablets were provided first with a film coating in a conventional manner followed by a sugar coating also in a conventional manner to give sugar-coated tablets.

Preparation 18 (Troches)

A uniform mixture composed of 116.0 g of lactose, 116.0 g of sucrose, 18.0 g of tragacanth powder, 1.0 ml of peppermint oil and a small amount of an antiseptic agent was thoroughly kneaded with admixture of an aqueous solution of 0.3 g of protease F-III-1-HM-27 in 40 ml of distilled water. Thus kneaded mixture was spread by use of a rolling pin on a glass plate dusted with potato starch into a sheet-like form of about 5 mm thickness, which was punched out with a die into pieces of a troche form followed by drying after keeping for 10 to 24 hours in a refrigerator to give troches each weighing 1 g and containing the protease.

Preparation 19 (Troches)

Sugar granules were prepared with 970 g of powdered sucrose wetted with about 110 g of ethyl alcohol followed by drying at 35° C. or below. These sugar granules were blended with a uniform powdery mixture of 1 g of protease F-III-2-HM-89 and 20 g of dry lactose and further with 10 g of magnesium stearate and the well kneaded mixture was shaped into troche forms each weighing 1 g by use of a die of 15 mm diameter.

Preparation 20 (Troches)

A mixture of 500 g of sorbitol and 500 g of polyethylene glycol 6000 containing 2 g of saccharin sodium and a small amount of a flavor was admixed with a powdery mixture of 3 g of protease F-III[1] and 20 g of dextrin followed by further admixture of 10 g of magnesium stearate. This mixture was well kneaded and shaped into troches each weighing 1 g and containing the protease.

Preparation 21 (Buccal tablets)

Buccal tablets containing protease F-I[1] and each weighing 1 g were prepared by substantially the same procedure and the same formulation as in Preparation 20 excepting the reduction of the amount of saccharin sodium to 0.2 g and replacement of protease F-III[1] with the same amount of protease F-I[1].

Preparation 22 (Ointment)

A mixture composed of 5 g of purified lanolin, 5 g of white beeswax and 89.6 g of white petrolatum was liquefied by melting and admixed with small amounts of an antiseptic agent and an antioxidant followed by cooling. Then, 0.4 g of protease F-I-1-HM-54 was added thereto followed by homogenization into an ointment containing the protease.

Preparation 23 (Ointment)

An ointment containing protease F-0-HM-45 was prepared by substantially the same procedure as in Preparation 22 according to the following formulation.

| | |
|---|---|
| Protease F-0-HM-45 | 0.2 g |
| Solid paraffin | 20.0 |
| Microcrystalline wax | 10.0 |
| Isopropyl myristate | 69.8 |
| Total | 100 g |

Preparation 24 (Ointment)

An ointment containing protease F-I[1] was prepared by substantially the same procedure as in Preparation 22 according to the following formulation.

| | |
|---|---|
| Protease F-I[1] | 0.5 g |
| Polyethylene glycol 400 | 57.0 |
| Polyethylene glycol 1500 | 20.0 |
| Polyethylene glycol 4000 | 22.5 |
| Total | 100 g |

Preparations 25A to 25F

The medicament forms shown by the following formulations 25A to 25F should be completed before use by admixing small amounts of an antiseptic agent, an antioxident and a flavor.

| Formulation 25A (Ointment) | |
|---|---|
| Protease F-I[2] | 0.6 g |
| Ethyl p-hydroxybenzoate | 0.1 |
| Butyl p-hydroxybenzoate | 0.1 |
| Lauromacrogol | 0.5 |
| Sorbitan sesquioleate | 5.0 |
| Cetanol | 18.0 |
| White petrolatum | 40.0 |
| Purified water | 35.7 |
| Total | 100 g |
| Formulation 25B (Ointment) | |
| Protease F-II[1] | 0.5 g |
| Cetanol | 15.0 |
| White petrolatum | 40.0 |
| Emalgen 408 | 2.0 |
| Emasol 310 | 3.0 |
| Purified water | 39.5 |
| Total | 100 g |
| Formulation 25C (Ointment) | |
| Protease F-I[1] | 0.5 g |
| Carboxymethyl cellulose, high-viscosity type | 2.0 |
| Glycerin | 80.0 |
| Purified water | 17.5 |
| Total | 100 g |
| Formulation 25D (Lotion) | |
| Protease F-III[1] | 0.5 g |
| Calamine | 8.0 |
| Sodium alginate | 1.25 |
| Zinc oxide | 8.0 |
| Glycerin | 4.0 |
| Methyl p-hydroxybenzoate | 0.2 |
| Tween 20 | 0.01 |
| Add purified water to make a total volume of 100 ml. | |
| Formulation 25E (Lotion) | |
| Protease F-I-2-HM-15 | 0.3 g |
| Stearyl alcohol | 2.1 g |
| Liquid paraffin | 40.0 ml |
| Sodium laurylsulfate | 1.0 g |
| Span 20 | 5.5 g |
| Tween 20 | 2.5 g |
| Methyl p-hydroxybenzoate | 0.025 g |
| Propyl p-hydroxybenzoate | 0.015 g |
| Add purified water to make a total volume of 100 ml. | |
| Formulation 25F (Liniment) | |
| Protease F-0-HM-45 | 0.2 g |
| Castor oil | 50.0 ml |
| Span 80 | 7.0 ml |
| Add a 0.67% aqueous solution of Tween 80 to make a total volume of 100 ml. | |

Preparation 26 (Suppository)

A mixture of 27.0 g of Witepsol E-85 and 72.7 g of Witepsol W-35 was melted into a homogeneous mixture and then further admixed with a small volume of a solution containing 0.05 g of methyl p-hydroxybenzoate and 0.05 g of butyl p-hydroxybenzoate as the antiseptic agents in propylene glycol followed by the admixture of 0.2 g of powdery protease F-III-2-HM-89 at about 50° C. The mixture in a molten state was mixed well and cast in an aluminum mold followed by cooling to give a solidified suppository form.

Preparation 27 (Suppository)

A mixture composed of 57.6 g of gelatin, 20.6 g of glycerin, 0.1 g of methyl p-hydroxybenzoate, 0.02 g of propyl p-hydroxybenzoate, 0.14 g of ethyl vanillin, 3.0 g of a 40:60 by weight mixture of titanium dioxide and glycerin, 0.6 g of Yellow No. 5 lake and 10 g of purified water was melted together followed by admixture of an aqueous solution prepared by dissolving 0.3 g of protease F-I[1] in 7.64 g of purified water and a suppository form of this mixture was prepared in the same manner as in Preparation 26.

Preparation 28 (Oral liposome medicament)

Egg yellow lecithin, cholesterol and diacetyl phosphate were mixed together in a weight ratio of 7:2:1 and 100 mg of this mixture taken in a flask were dissolved in 8 ml of chloroform followed by the evaporation of the solvent to leave a thin film of the mixture on the walls of the flask. This film was mixed with 13 ml of a phosphate buffer solution at a pH of 7.2 containing 100 mg of protease F-III-2-HM-89 and, after thorough shaking, the mixture was subjected to an ultrasonic treatment. About 1 hour after the end of the ultrasonic treatment, the mixture was centrifuged for 1 hour at 50,000 G followed by twice of washing with the same buffer solution but containing no protease. The thus obtained precipitates were suspended in 2 ml of a physiological saline solution followed by removal of microorganisms from the suspension to give an oral liposome medicament which was storable at 0° to 5° C. and usable by suitable dilution before use for a medical treatment.

Preparation 29 (Oral liposome medicament)

A solution of 85 mg of egg yellow lecithin and 15 mg of cholesterol in 8 ml of chloroform was spread on the walls of a flask and evaporation of the solvent left a thin film of the mixture on the walls. This film was mixed with 15 ml of a phosphate buffer solution at a pH of 7.2 containing 100 mg of protease F-0-HM-45 and 50 mg of albumin and the mixture was subjected to an ultrasonic treatment. After about 30 minutes of standing, the mixture was centrifuged for 30 minutes at 100,000 G followed by twice of washing with the same buffer solution but containing no protease and albumin. The thus obtained precipitates were suspended in 2 ml of a physiological saline solution followed by removal of microorganisms to give an oral liposome medicament which was storable at 0° to 5° C. and usable by suitable dilution before use for a medical treatment.

Preparation 30 (Oral liposome medicament)

A solution of 100 mg of soybean lecithin composed of 25.4% of campesterol, 26.4% of stigmasterol and 48.2% of β-sitosterol in 5 ml of chloroform was spread on the walls of a flask and evaporation of the solvent from the mixture left a thin film of the lecithin on the walls. Into the flask were added 15 ml of a phosphate buffer solution at a pH of 7.2 containing 120 mg of protease F-I[1] and 50 mg of mannitol and the mixture was thoroughly shaken and subjected to an ultrasonic treatment. After about 1 hour of standing, the thus obtained suspension was centrifuged for 2 hours at 35,000 G followed by twice of washing with the same buffer solution but containing no protease and mannitol. The precipitates were collected and suspended in 1 ml of a physiological saline solution followed by removal of microorganisms to give an oral liposome medicament containing the protease which was storable at 0° to 5° C. and usable by suitable dilution before use for a medical treatment.

Preparation 31 (Oral liposome medicament)

A solution of 5 mg of phosphatidic acid, 45 mg of soybean lecithin and 50 mg of egg yellow lecithin in 5 ml of chloroform was spread on the walls of a flask and evaporation of the solvent left a thin film of the mixture on the walls. Into the flask were added 5 ml of a phosphate buffer solution at a pH of 7.2 containing 100 mg of protease F-I-2-HM-15, 50 mg of dextrin and 10 mg of lysine and an oral liposome medicament containing the protease was prepared in the same manner as in Preparation 28. This medicament was storable at 0° to 5° C. and usable by suitable dilution before use for a medical treatment.

Preparation 32 (Oral liposome medicament)

A solution of 100 mg of egg yellow lecithin in 5 ml of chloroform was spread on the walls of a flask and evaporation of the solvent left a thin film of lecithin on the walls. Into the flask were added 5 ml of a phosphate buffer solution at a pH of 7.2 containing 100 mg of protease F-III[1], 40 mg of mannit and 20 mg of arginine and an oral liposome medicament containing the protease was prepared in the same manner as in Preparation 28. This medicament was storable at 0° to 5° C. and usable by suitable dilution before use for a medical treatment.

Preparation 33 (Oral liposome medicament)

A solution of a mixture composed of 35 mg of phosphatidyl ethanolamine, 20 mg of phosphatidyl inositol, 35 mg of phosphatidyl serine and 10 mg of cholesterol in 10 ml of chloroform was spread on the wall of a flask and evaporation of the solvent left a thin film of the mixture on the walls. Into the flask were added 5 ml of a phosphate buffer solution at a pH of 7.2 containing 100 mg of protease F-III-1-HM-27 and 200 mg of hydroxyethylated starch and 20 mg of polyvinyl pyrrolidone as the stabilizers and an oral liposome medicament containing the protease was prepared in the same manner as in Preparation 28. This medicament was storable at 0° to 5° C. and usable by suitable dilution before use for a medical treatment.

Preparation 34 (Oral liposome medicament)

A solution of 100 mg of egg yellow lecithin containing 5% of phosphatidyl ethanolamine and 10% of sphingomyelin and 10 mg of chenodeoxycholic acid in 10 ml of chloroform was spread on the walls of a flask and evaporation of the solvent left a thin film of the mixture on the walls of the flask. Into the flask were added 5 ml of a phosphate buffer solution at a pH of 7.2 containing 40 mg of protease F-II-HM-64, 20 mg of a blood plasma of human origin and 10 mg of sucrose and an oral liposome medicament containing the protease was prepared in the same manner as in Preparation 28. This medicament was storable at 0° to 5° C. and usable by suitable dilution before use for a medical treatment.

Preparation 35 (Oral liposome medicament)

A solution of 60 mg of soybean lecithin, 30 mg of ursodeoxycholic acid and 10 mg of egg yellow lecithin in 5 ml of chloroform was spread on the walls of a flask and evaporation of the solvent left a thin film of the mixture on the walls. Into the flask were added 5 ml of a phosphate buffer solution at a pH of 7.2 containing 100 mg of protease F-I$^2$, 30 mg of polyvinyl pyrrolidone and 15 mg of gelatin and the mixture was thoroughly shaken. An oral liposome medicament containing the protease was prepared with this mixture in the same manner as in Preparation 28. This medicament was storable at 0° to 5° C. and usable as a medicament for medical treatment.

Preparation 36 (Fine granules)

The components shown by the following formulation were uniformly mixed and the powdery mixture was shaped by use of a granulator into a medicament form of fine granules having a particle size to pass a screen of 30 mesh opening but not to pass a screen of 100 mesh opening by the Tyler standard series.

| | |
|---|---|
| Protease F-III-1-HM-27 | 0.2 g |
| Crystalline cellulose | 64.5 |
| Lactose | 15.0 |
| Potato starch | 15.0 |
| Hydroxypropyl cellulose | 3.0 |
| Polyvinyl pyrrolidone | 2.3 |
| Total | 100 g |

Preparation 37 (Fine granules)

The components shown by the following formulation were uniformly mixed and the powdery mixture was shaped by use of a granulator into a medicament form of fine granules having a particle size to pass a screen of 30 mesh opening but not to pass a screen of 100 mesh opening by the Tyler standard series.

| | |
|---|---|
| Protease F-III-1-HM-89 | 0.2 g |
| Crystalline cellulose | 55.0 |
| Mannitol | 26.8 |
| Corn starch | 15.0 |
| Methyl cellulose | 3.0 |
| Total | 100 g |

EXAMPLE 1

Live earthworms of the species Lumbricus rubellus weighing 84 g were added to a physiological saline solution to give a total volume of 300 ml and ground into a homogeneous suspension, which was incubated for 100 hours at 37° C. followed by centrifugal separation into an extract solution and insoluble residue. The residue was washed with 150 ml of the physiological saline solution and the washings were combined with the extract solution to give a total volume of 400 ml of the combined solution having a fibrinolytic activity of 375 mm$^2$/ml after 10 times dilution. The dehydrated material obtained from this combined solution by freeze-drying had a fibrinolytic activity of 142 mm$^2$/mg.

EXAMPLE 2

Live earthworms weighing 84 g were added to 500 ml of distilled water containing 0.3 g of phenol and ground into a homogeneous suspension which was incubated for 76 hours at 30° C. followed by filtration to remove the insoluble residue from the aqueous extract solution. The residue was washed with 200 ml of distilled water and the washings were combined with the extract solution to give a total volume of 650 ml of the combined solution having a fibrinolytic activity of 220 mm$^2$/ml after 10 times dilution.

EXAMPLE 3

Live earthworms weighing 84 g were added to an aqueous mixture of 400 ml of distilled water and 30 ml of ethyl alcohol and ground into a homogeneous suspension, which was incubated for 240 hours at 25° C. followed by centrifugal separation to give a clear extract solution having a fibrinolytic activity of 350 mm$^2$/ml after 10 times dilution.

EXAMPLE 4

An aqueous suspension was prepared by admixing 50 g of a powder of vacuum-dried earthworms with 400 ml of a physiological saline solution and 100 ml of a salt solution having a pH of 6.5 as prepared with a 1.8% aqueous solution of phosphoric acid and a 1.8% ammonia water and the suspension was incubated for 100 hours at 38° C. followed by filtration to give a clear extract solution having a fibrinolytic activity of 725 mm$^2$/ml after 10 times dilution corresponding to an activity of 72.5 mm$^2$/mg of the dry powder of earthworms.

EXAMPLE 5

An aqueous suspension was prepared by dispersing 50 g of a powder of freeze-dried earthworms in a mixture of 250 ml of a dilute salt solution having a pH of 6.3 as prepared with a 2% aqueous acetic acid solution and a 2% aqueous sodium hydroxide solution, 200 ml of a physiological saline solution and 50 ml of distilled water with admixture of 0.5 g of sodium azide and the suspension was incubated for 72 hours at 37° C. followed by filtration to give a clear extract solution having a fibrinolytic activity of 460 mm$^2$/ml after 10 times dilution.

EXAMPLE 6

An aqueous suspension was prepared by dispersing 50 g of a defatted powder of freeze-dried earthworms into a mixture of 200 ml of an acetate buffer solution having a pH of 7.0, 200 ml of a borate buffer solution having the same value of pH as above, 100 ml of distilled water, 10 ml of propyl alcohol and 10 ml of dioxane and the suspension was incubated for 240 hours at 32° C. followed by filtration to give a clear extract solution having a fibrinolytic activity of 772 mm$^2$/ml after 10 times dilution.

EXAMPLE 7

An aqueous suspension was prepared by dispersing 50 g of a defatted powder of freeze-dried earthworm bodies with the entrails removed into an aqueous mixture of 250 ml of a dilute salt solution having a pH of 6.8 as prepared with an aqueous acid mixture containing 1.8% of phosphoric acid and 3.5% of hydrogen chloride and a 2N aqueous solution of potassium hydroxide, 225 ml of a physiological saline solution and 25 ml of acetone and the suspension was incubated for 96 hours at 25° C. followed by filtration with suction to give a clear extract solution having a fibrinolytic activity of 600 mm²/ml after 10 times dilution.

EXAMPLE 8

An aqueous suspension was prepared by dispersing 10 g of a defatted powder of earthworms dehydrated by high-temperature flash drying into an aqueous mixture of 50 ml of a phosphate buffer solution having a pH of 6.4 and 50 ml of a citrate buffer solution having a pH of 6.5 and the suspension was incubated for 7 hours at 37° C. followed by filtration to give a clear extract solution. The residue was washed with a physiological saline solution and the washings were combined with the above extract solution to give a total volume of 120 ml of the combined solution. This combined extract solution was admixed with 0.1 g of sodium azide and further incubated for 10 hours at 37° C. The resultant solution had a fibrinolytic activity of 280 mm²/ml after 10 times dilution.

EXAMPLE 9

An aqueous suspension was prepared by dispersing 10 g of a defatted powder of freeze-dried earthworms into an aqueous mixture of 50 ml of a phosphate buffer solution having a pH of 7.4 and 50 ml of a physiological saline solution and the suspension was agitated for 4 hours at 22° C. to effect extraction of the water-soluble ingredients into the aqueous solution followed by centrifugal separation to give a clear extract solution. The fibrinolytic activity of this extract solution was, after admixture of 0.07 g of sodium azide and incubation for 5 hours at 37° C., 190 mm²/ml after 10 times dilution.

EXAMPLE 10

Live earthworms weighing 10 g were added to an aqueous mixture of 70 ml of an acetate buffer solution having a pH of 7.0 and 30 ml of distilled water and ground into a homogeneous aqueous suspension which was agitated for 2 hours at 20° C. to effect extraction of the water-soluble ingredients into the aqueous solution followed by centrifugal separation to give a clear extract solution. The residue was washed with water and the washings were combined with the extract solution to give a total volume of 180 ml of the combined solution having a fibrinolytic activity of, after admixture of 0.1 g of sodium azide and incubation for 7 hours at 37° C., 40 mm²/ml after 10 times dilution.

EXAMPLE 11

An aqueous suspension prepared by dispersing 1 kg of a freeze-dried powder of earthworms in 10 liters of an aqueous solution containing 0.1% by weight of sodium benzoate and 0.9% by weight of sodium chloride was agitated for 96 hours at 32° C. to extract the water-soluble ingredients followed by filtration. The residue from the above filtration was washed with 3 liters of the same aqueous solution of sodium benzoate and sodium chloride as above and the washings were combined with the filtrate to give 12.5 liters of a clear extract solution having a fibrinolytic activity of 490 mm²/ml after 10 times dilution.

The thus obtained extract solution was concentrated to a total volume of 0.5 liter by ultrafiltration and the concentrated solution was subjected to fractional precipitation by first adding 0.5 liter of ethyl alcohol thereto to obtain precipitates and then by adding a further volume of ethyl alcohol to the filtrate from the first precipitation to give a final ethyl alcohol concentration of 80% so that an additional amount of precipitates was obtained. The precipitates obtained in the above two-step precipitation were combined and washed with ethyl alcohol followed by vacuum-drying to give 40.5 g of a dry powder having a fibrinolytic activity of 1285 mm²/mg.

The above obtained powder was dissolved in 1 liter of a 10mM phosphate buffer solution having a pH of 8.0 and the solution was passed through a column filled with a hexyl-Sepharose prepared by the reaction of hexylamine with agarose activated with epichlorohydrin (Sepharose, a product by Pharmacia Fine Chemicals Co.) to have the active ingredients adsorbed thereon. After washing with the same buffer solution as above, elution of the column was undertaken with the same buffer solution as above but containing sodium chloride in a concentration of 0.25M as the eluant to give 1 liter of an eluate solution.

The eluate solution was, after dialysis, dehydrated by freeze-drying to give 5.75 g of a dehydrated material having a fibrinolytic activity of 7241 mm²/mg.

EXAMPLE 12

The procedure down to the fractional precipitation with ethyl alcohol followed by vacuum-drying was substantially the same as in Example 11 above and 47 g of the dried powder having a fibrinolytic activity of 1100 mm²/mg were dissolved in 1 liter of a 20mM phosphate buffer solution having a pH of 7.0. This solution was passed through a column filled with an ETI (albumen trypsin inhibitor)-Sepharose prepared by combining an albumen trypsin inhibitor (a product by Sigma Co.) to agarose activated with epichlorohydrin to have the active ingredients adsorbed thereon. After washing first with the same buffer solution as above and then with a 0.1M acetate buffer solution having a pH of 5.0, elution of the column was undertaken with the same acetate buffer solution as above but containing sodium chloride and alginine in concentrations of 1M and 0.5M, respectively, as the eluant to give 0.8 liter of an eluate solution.

The eluate solution was, after dialysis, dehydrated by freeze-drying to give 255 mg of a dehydrated material having a fibrinolytic activity of 70,960 mm²/mg.

EXAMPLE 13

An aqueous dispersion of 1 kg of a powder of freeze-dried earthworms in 10 liters of an aqueous salt solution containing 0.1% of sodium benzoate and 0.9% of sodium chloride was agitated for 72 hours at 30° C. to effect extraction of the water-soluble ingredients into the aqueous solution followed by filtration to give a clear extract solution. The residue was washed with 3 liters of the same salt solution as above and the washings were combined with the extract solution to give a total volume of 13 liters of the clear combined solution having a fibrinolytic activity of 450 mm²/ml after 10 times dilution.

The above obtained aqueous solution was concentrated by ultrafiltration into a liquid volume of 0.71 liter and then admixed with equal volume of ethyl alcohol to precipitate solid material which was collected by filtration. The filtrate was further admixed with ethyl alcohol to give a final concentration of ethyl alcohol of 80% to give further precipitates which were collected and washed with ethyl alcohol followed by vacuum-drying into a dry powder. The total yield of the dry powdery products in the above two-step precipitation was 42 g and the fibrinolytic activity thereof was 1322 mm²/mg.

Figure 44:
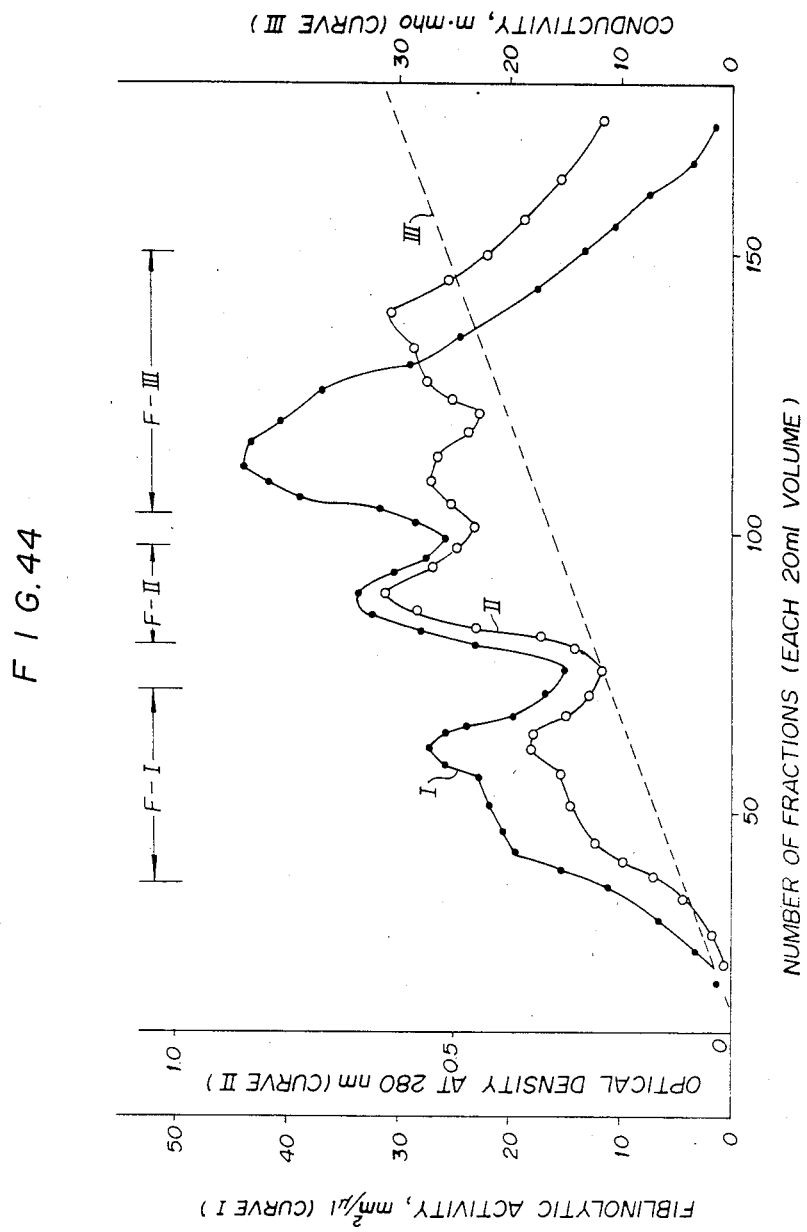
FIG. 44 shows the fibrinolytic activity and the optical density at 280 nm of the fractions obtained in the column chromatographic fractionation of the earthworm extract in Example 13.

The above obtained powdery product was dissolved in 1000 ml of distilled water and subjected to column-chromatographic fractionation by use of an adsorbent of DEAE-Cellulofine (a product by Chisso Co.) to give three fractions F-I, F-II and F-III. FIG. 44 gives the results of the fibrinolytic activity in mm² and the optical density at 280 nm of the eluate fractions each in a 20 ml volume obtained in the above mentioned column chromatography by the curves I and II, respectively. The broken line in FIG. 44 indicates the concentration of sodium chloride in the eluate fractions given by the electric conductivity in m.mho.

Each of the fractions F-I to F-III was subjected to a treatment of salting-out by 60% saturation with ammonium sulfate and the precipitates were dissolved in a small volume of a 10 mM phosphate buffer solution having a pH of 8.0. The solution was successively subjected to gel filtration with Sephacryl S-200 and desalting concentration by ultrafiltration followed by freeze-drying to give 629 mg, 879 mg or 1070 mg of the purified proteases having a fibrinolytic activity of 13,780 mm²/mg, 9,290 mm²/mg or 17,620 mm²/mg from the fractions F-1, F-II and F-III, respectively. These purified protease fractions are called proteases F-I$^2$, F-II$^1$ and F-III$^1$, respectively.

The plasminogen activator activity was examined for each of the above obtained purified proteases. Thus, the purified protease was dissolved in water in a concentration of 0.1 mg/ml and 20 μl of this solution were admixed with 10 μl of the plasminogen having an activity of 5 units/ml (a product by Sigma Co.) and 30 μl of a 0.17M borate buffer solution having a pH of 7.8 and containing 0.01M sodium chloride and, after standing for 10 minutes at 37° C., 0.03.ml of the mixed solution was dropped vertically on to a fibrin plate free of plasminogen (a product by Miles Laboratories, Inc.). The area in mm² of the dissolved portion was determined on the plate after 18 hours of the reaction at 37° C. When the above obtained area was taken as X and the corresponding area in mm² obtained by use of 10 μl of the 0.17M borate burrer solution in place of the plasminogen was taken as Y, then the plasminogen activator activity is expressed by X-Y. The values of the thus determined plasminogen activator activity were 2025 mm²/mg, 1721 mm²/mg and 1283 mm²/mg for the dehydrated products obtained from the fractions F-I$^2$, F-II$^1$ and F-III$^1$, respectively.

The values of the molecular weight as determined by the gel filtration method and the pH at the isoelectric point of these protease fractions were as follows: about 22,000 and 4.0 for protease F-I$^2$; about 23,000 and 3.8 for protease F-II$^1$; and about 28,000 and 3.7 for protease F-III$^1$.

EXAMPLE 14

The purified proteases obtained in Example 13 were examined for the reactivity with fibrin and fibrinogen. Thus, 0.18 ml of blood plasma of human, 0.02 ml of a 250 mM aqueous solution of calcium chloride and 0.02 ml of an aqueous solution of one of the purified proteases in a varied concentration were mixed and the FDP (fibrindecomposition peptide) produced by the reaction for 30 minutes at 37° C. in the above mixture was determined by the latex coagulation test using a kit for the thromboWellco test (manufactured by Wellcome Co.). The results are shown in Table 8 in the columns under the heading of CaCl$_2$ (+) for 5 different concentrations of $10^4$ to $10^{-1}$ ng/ml. The marks (+), (++) and (+++) in the table indicate the formation of FDP from fibrin, the increase of the number of the + marks corresponding to the increase in the formation of FDP, while the mark (−) indicates the absence of formation of FDP from fibrin for each concentration.

On the other hand, the same test as above was repeated in the absence of calcium chloride, i.e. by the use of a physiological saline solution in place of the aqueous solution of calcium chloride, to find that no FDP was formed irrespective of the protease fraction and the concentration thereof as is shown in the columns of Table 8 under the heading of CaCl$_2$ (−). These results support the conclusion that the proteases of the invention have reactivity with fibrin but not with fibrinogen.

TABLE 8

| Concentration of purified protease | F - I$^2$ | | F - II$^1$ | | F - III$^1$ | |
|---|---|---|---|---|---|---|
| | | | CaCl$_2$ | | | |
| | (+) | (−) | (+) | (−) | (+) | (−) |
| $10^4$ ng/ml | − | − | + | − | +++ | − |
| $10^3$ | − | − | +++ | − | +++ | − |
| $10^2$ | − | − | +++ | − | + | − |
| 10 | + | − | +++ | − | + | − |
| 1 | + | − | +++ | − | +++ | − |
| $10^{-1}$ | + | − | ++ | − | + | − |

EXAMPLE 15

Each of the freeze-dried purified proteases of the fractions F-I$^2$ to F-III$^1$ in Example 13 was orally administrated to healthy men in a dose of 1 μg/kg body weight and the peripheral blood of each of the subjects was taken periodically to give the euglobulin fractions, with which measurements were undertaken for the time of complete dissolution of euglobulin in hours and the fibrin dissolving activity in mm² by the standard fibrin plate test. The results are shown in FIGS. 45a and 45b, respectively.

Figure 45A:
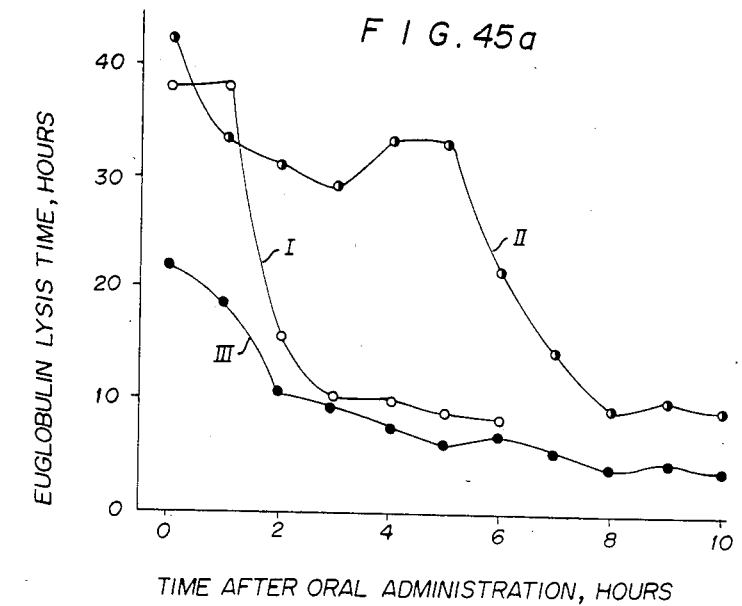
FIGS. 45a and 45b show the euglobulin dissolving time and the fibrin dissolving activity, respectively, of the peripheral blood of men orally administrated with the protease fractions (see Example 15).

As is shown in FIG. 45a, the time for the solubilization of euglobulin was remarkably decreased about 2 hours after the oral administration of the purified proteases of F-I$^2$ (curve I) and F-III$^1$ (curve III) and the decrease in the time of euglobulin solubilization continued sustainedly. On the other hand, the time for the euglobulin solubilization began to gradually decrease about 6 hours after the oral administration of the purified protease F-II$^1$ (curve II). These results support the conclusion that each of the proteases F-I$^2$ to F-III$^1$ has an effect to enhance the fibrinolytic activity of the peripheral blood of human when administrated orally.

Figure 45B:
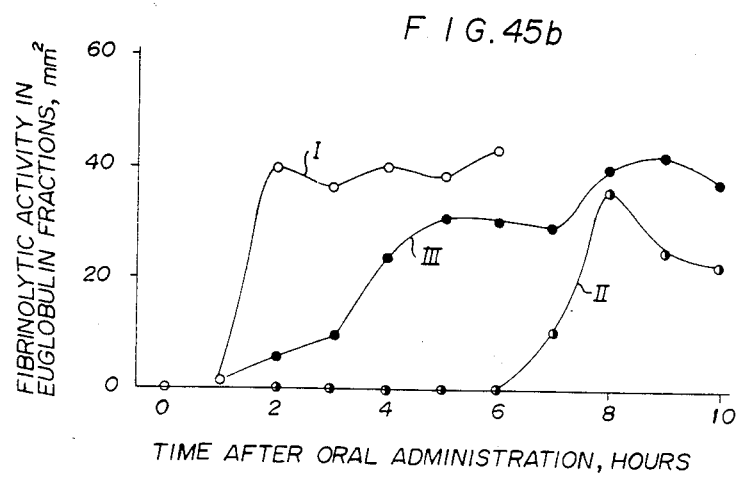

Further, FIG. 45b indicates that, though with considerable differences between individuals, the fibrinolytic activity of the euglobulin fractions obtained from the peripheral blood was maximum at 2 to 7 hours after the oral administration of the proteases F-I$^2$ to F-III$^1$ (curves I to III, respectively) to the subjects and the fibrinolytic activity thereof was kept sustainedly even 10 hours after administration.

EXAMPLE 16

Figure 46:
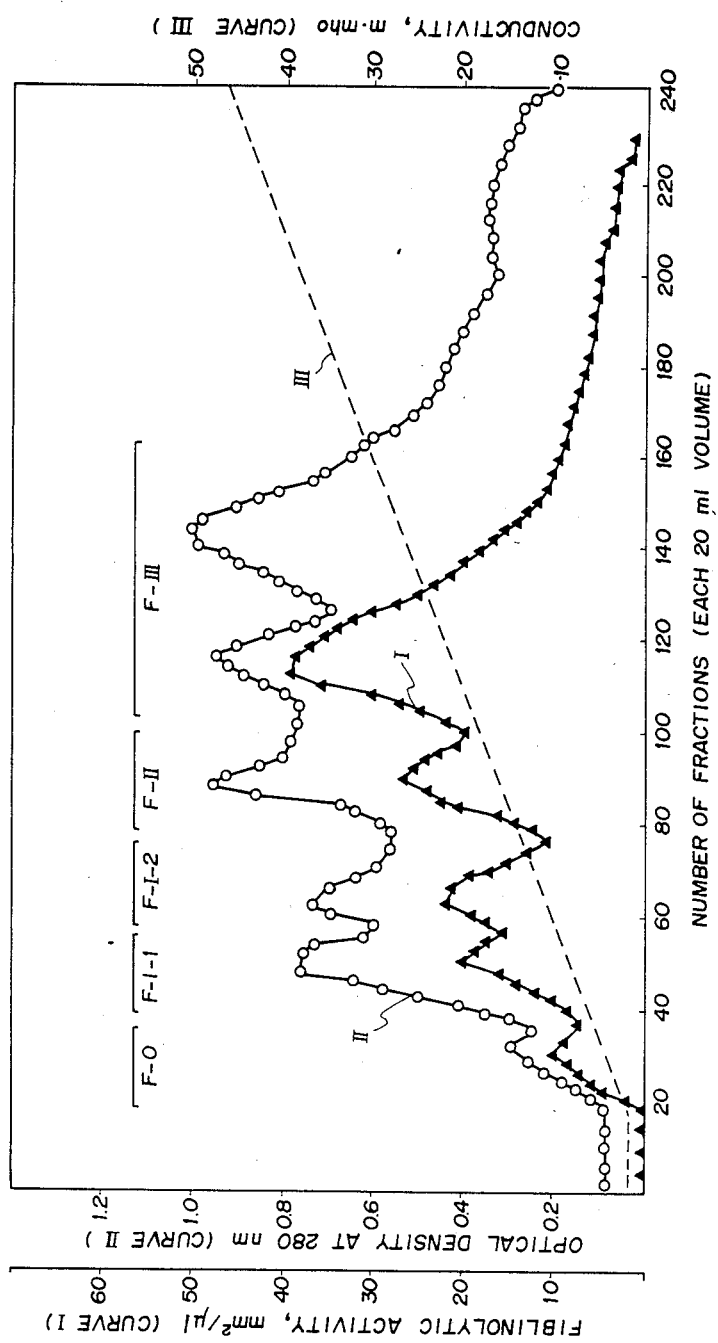
FIG. 46 shows the fibrinolytic activity and the optical density at 280 nm of the fractions obtained in the column chromatographic fractionation of the earthworm extract in Example 16.

The same extraction procedure as in Example 13 was repeated and 42 g of a vacuum-dried powder of crude extract having a fibrinolytic activity of about 1322 mm²/mg were obtained. This powder was dissolved in 1000 ml of purified water and the aqueous solution was subjected to column chromatography by use of DEAE-Cellulofine to give 5 fractions F-0, F-I-1, F-I-2, F-II and F-III as shown in FIG. 46.

Each of the above obtained 5 fractions was subjected to purification in the same manner as in Example 13 including salting-out, gel filtration, ultrafiltration and freeze-drying to give 5 purified protease fractions of 0.07 g of F-0 mainly composed of protease HM-45, 0.209 g of F-I-1 mainly composed of protease HM-54, 0.420 g of F-I-2 mainly composed of protease HM-15, 0.879 g of F-II[1] and 1.070 g of F-III[1]. The fibrinolytic activities of these purified protease fractions for coagulated fibrin were 8,816 mm$^2$/mg, 15,200 mm$^2$/mg, 12,000 mm$^2$/mg, 9,290 mm$^2$/mg and 17,620 mm$^2$/mg for F-0, F-I-1, F-1-2, F-II[1] and F-III[1], respectively.

EXAMPLE 17

The same procedures was repeated as in the preceding example down to the column chromatographic fractionation to give the eluate solutions corresponding to the fractions F-0, F-I-1, F-I-2, F-II and F-III and each of the first three fractions was passed through a column filled with DEAE-Cellulofine equilibrated with a 10 mM phosphate buffer solution having a pH of 8.0 so as to have the active ingredients adsorbed on the adsorbent. The active ingredients were eluted out by the elution with the same buffer solution at a concentration gradient of 0 to 100 mM of sodium chloride and the active fractions were subjected to gel filtration with Sephadex G-75 to give purified proteases of 0.02 g of HM-45, 0.07 g of HM-54 and 0.06 g of HM-15 from the fractions F-0, F-I-1 and F-I-2, respectively, each behaving as a single component material by the electrophoresis with a polyacrylamide gel.

The eluate solution for the fraction F-II was passed through a column filled with Toyopearl HW-55 (a product by Toyo Soda Co.) equilibrated with a 30%-saturated aqueous solution of ammonium sulfate to have the active ingredients adsorbed thereon followed by elution at a concentration gradient of 30% to 10% saturation with ammonium sulfate. A solution of combined eluate fractions containing active ingredients was desalted and passed through a column filled with Hexyl-Sepharose equilibrated with a 10 mM phosphate buffer solution having a pH of 6.0 so as to have the active ingredients adsorbed thereon. The fractions obtained by the subsequent elution of the active ingredients with the same buffer solution at a concentration gradient of 0 to 150 mM of sodium chloride were combined and subjected to gel filtration with Sephadex G-75 to give 0.10 g of the purified protease HM-64 behaving as a single component material by the electrophoresis with a polyacrylamide gel.

Figure 47:
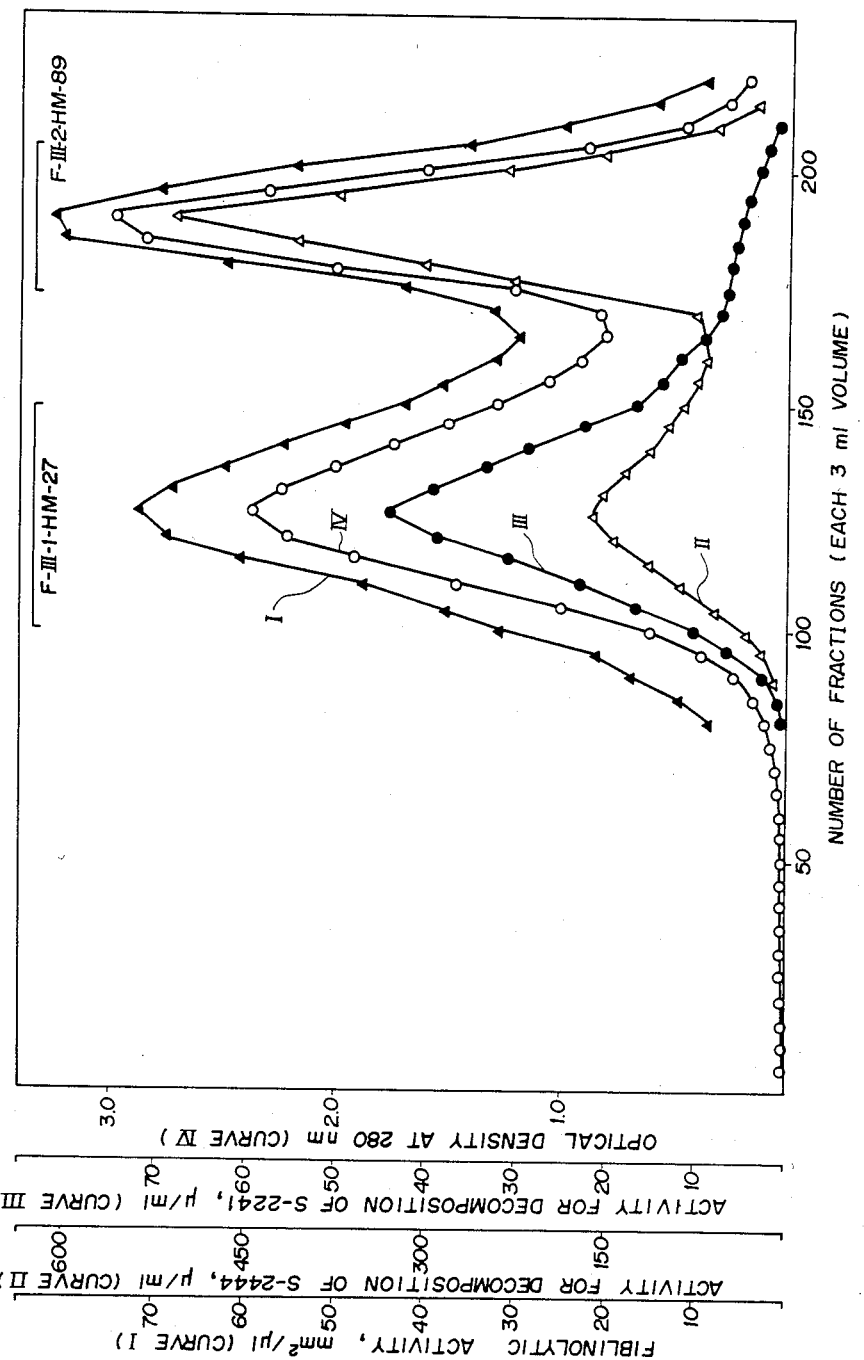
FIG. 47 shows the elution curves in the column chromatographic purification of proteases HM-27 and HM-89 in Example 17.

The eluate solution for the fraction F-III was passed through a column filled with Sepharose affinity carrier bearing albumin trypsin inhibitor (a product by Sigma Co.) and equilibrated with a 20 mM phosphate buffer solution having a pH of 8.0 so as to have the active ingredients adsorbed thereon followed by washing with a 0.1M acetate buffer solution having a pH of 5.0 and containing 1M of sodium chloride. Subsequent elution of the active ingredients with an acetate buffer solution containing 1M of sodium chloride and 0.5M of arginine gave a fraction F-III[1] which was further purified by column chromatography by passing through a column filled with Toyopearl HW-55 equilibrated with a saturated aqueous solution of ammonium sulfate followed by elution at a concentration gradient of 30% to 10% saturation with ammonium sulfate to give 0.070 g of a purified protease HM-27 and 0.060 g of protease HM-89 each behaving as a single component material by the electrophoresis with a polyacrylamide gel. FIG. 47 shows the elution curves in this final column chromatography as given by the fibrinoloytic activity, the activities for S-2444 and S-2251 and the absorbance at 280 nm for the fractions each in a volume of 3 ml.

EXAMPLE 18

Five fractions of F-0, F-I-1, F-I-2, F-II and F-III were obtained in substantially the same manner as in Example 16 after column chromatographic fractionation with DEAE-Cellulofine. Each of the fractions was subjected to salting-out with 90% saturation of magnesium sulfate to give precipitates, which were dissolved in a small volume of a 10 mM phosphate buffer solution having a pH of 8.0 followed by the gel filtration with Sephacryl S-200, desalting concentration by ultrafiltration and freeze-drying to give 0.04 g of a purified fraction F-0 mainly composed of HM-45, 0.170 g of a fraction F-I-1 mainly composed of HM-54, 0.260 g of a fraction F-I-2 mainly composed of HM-15, 0.530 g of a fraction F-II[1] or 0.650 g of a fraction F-III[1] having a fibrinolytic activity of 9,210, 16,300, 13,000, 10,200 or 18,900 mm$^2$/mg, resptively.

EXAMPLE 19

One kilogram of a freeze-dried powder of earthworms was dispersed in 10 liters of an aqueous solution containing 0.9% of sodium chloride and 0.02% of ethyl 4-hydroxybenzoate and the dispersion was agitated at 30° C. for 96 hours. The dispersion was then filtered and the residue was washed with 3 liters of an aqueous solution containing 0.9% of sodium chloride and 0.01% of ethyl 4-hydroxybenzoate. The washings were combined with the filtrate in the first filtration to give 13 liters of a clear extract solution having a fibrinolytic activity for coagulated fibrin of 450 mm$^2$/ml after 10 times dilution. The liquid volume of this extract solution was reduced to 0.71 liter by ultrafiltration followed by the addition of 0.47 liter of acetone to obtain precipitates. After filtration to separate the precipitates, the filtrate was further admixed with acetone to give 70% of acetone in the final solution to obtain an additional amount of precipitates, which were combined with the precipitates obtained in the first precipitation and washed again with acetone followed by vacuum drying to give 40 g of dried powdery product having a fibrinolytic activity for coagulated fibrin of 1310 mm$^2$/mg.

The above obtained powdery product was dissolved in 1 liter of purified water and the aqueous solution was fractionated by column chromatography with DEAE-Cellulofine as the adsorbent into five fractions of F-0, F-I-1, F-I-2, F-II and F-III containing novel proteases. Each of these fractions was further purified in substantially the same manner as in Example 17 to give 0.019 g of HM-45, 0.067 g of HM-54, 0.057 g of HM-15, 0.095 g of HM-64 or 0.067 g of HM-27 and 0.057 g of HM-89 each behaving as a single component material by the electrophoresis with a polyacrylamide gel from the fractions F-0, F-I-1, F-I-2, F-II or F-III, respectively.

EXAMPLE 20

The first portion of the extraction procedure in Example 16 was repeated to give 0.71 liter of a clear concentrated extract solution after ultrafiltration. The extract solution was admixed with 0.47 liter of propyl alcohol to obtain precipitates which were separated by filtration. The filtrate was further admixed with propyl alcohol to give a 60% concentration in the final solution and the precipitates obtained in this second precipitation were combined with those obtained in the first precipitation and washed with propyl alcohol followed by vacuum drying to give 34 g of a dry powdery product having a fibrinolytic activity for coagulated fibrin of 1280 mm$^2$/mg.

This powdery product was dissolved in 1 liter of purified water and the aqueous solution was fractionated by column chromatography with DEAE-Sepharose into five fractions of F-0, F-I-1, F-I-2, F-II and F-III containing novel proteases. Each of these fractions was further purified in substantially the same manner as in Example 17 to give 0.018 g of HM-45, 0.063 g of HM-54, 0.054 g of HM-15, 0.090 g of HM-64 or 0.063 g of HM-27 and 0.054 g of HM-89 each behaving as a single component material by the electrophoresis with a polyacrylamide gel from the fractions F-0, F-I-1, F-I-2, F-II or F-III, respectively.

EXAMPLE 21

The first portion of the extraction procedure in Example 16 was repeated to give 0.71 liter of a clear concentrated extract solution after ultrafiltration. The extract solution was admixed with 0.47 liter of isopropyl alcohol to obtain precipitates which were separated by filtration. The filtrate was further admixed with isopropyl alcohol to give a 60% concentration thereof in the final solution and the precipitates obtained in this second precipitation were combined with those obtained in the first precipitation and washed with isopropyl alcohol followed by vacuum drying to give 37 g of a dry powdery product having a fibrinolytic activity of 1300 mm$^2$/mg.

This powdery product was dissolved in 1 liter of purified water and the aqueous solution was fractionated by column chromatography with DEAE-Cellulofine into five fractions of F-0, F-I-1, F-I-2, F-II and F-III. Each of these fractions was further purified in substantially the same manner as in Example 17 to give 0.017 g of HM-45, 0.060 g of HM-54, 0.050 g of HM-15, 0.085 g of HM-64 or 0.060 g of HM-27 and 0.050 g of HM-89 each behaving as a single component material by the electrophoresis with a polyacrylamide gel from the fractions F-0, F-I-1, F-I-2, F-II or F-III, respectively.

EXAMPLE 22

The first portion of the extraction procedure in Example 16 was repeated to give 0.71 liter of a clear concentrated extract solution after ultrafiltration and the extract solution was subjected to salting-out by 60% saturation with ammonium sulfate to precipitate the active ingredients. The precipitates were dissolved in 1 liter of purified water and the aqueous solution was, after dialysis, fractionated by column chromatography with DEAE-Cellulofine into five fractions of F-0, F-I-1, F-I-2, F-II and F-III containing novel proteases. Each of these fractions was further purified in substantially the same manner as in Example 17 to give 0.020 g of HM-45, 0.068 g of HM-54, 0.057 g of HM-15, 0.100 g of HM-64 or 0.065 g of HM-27 and 0.058 g of HM-89 each behaving as a single component material by the electrophoresis with a polyacrylamide gel from the fractions F-0, F-I-1, F-I-2, F-II or F-III, respectively.

EXAMPLE 23

The first portion of the extraction procedure in Example 16 was repeated to give 13 liters of an extract solution of earthworms having a fibrinolytic activity for coagulated fibrin of 540 mm$^2$/ml after 10 times dilution. This extract solution was weakly acidified to have a pH of 4.0 by the addition of a 1M aqueous solution of acetic acid and passed through a column filled with Amberlite CG-50 equilibrated in advance with a 0.1M acetate buffer solution having a pH of 4.0 to have the active ingredients adsorbed thereon. After washing with the same buffer solution, elution of the active ingredients was performed with a 0.1M acetate buffer solution having a pH of 5.5. The eluate solution exhibiting activity was admixed with a 0.5N aqueous solution of sodium hydroxide to have a pH of 8.0 and desalted and concentrated by ultrafiltration followed by column chromatographic fractionation with DEAE-Cellulofine into five fractions of F-0, F-I-1, F-I-2, F-II and F-III containing novel proteases. Each of these fractions was further purified in substantially the same manner as in Example 17 to give 0.015 g of HM-45, 0.050 g of HM-54, 0.040 g of HM-15, 0.065 g of HM-64 or 0.050 g of HM-27 and 0.040 g of HM-89 each behaving as a single component material by the electrophoresis with a polyacrylamide gel from the fractions F-0, F-I-1, F-I-2, F-II or F-III, respectively.

EXAMPLE 24

The first portion of the extraction procedure in Example 16 was repeated to give 42 g of a dry powdery product having a fibrinolytic activity for coagulated fibrin of 1322 mm$^2$/mg after fractional precipitation with ethyl alcohol and vacuum-drying. This powdery product was dissolved in 1 liter of purified water and the aqueous solution was fractionated by column chromatography with TEAE-cellulose into five fractions of F-0, F-I-1, F-I-2, F-II and F-III containing novel proteases. Each of these fractions was further purified in substantially the same manner as in Example 17 to give 0.022 g of HM-45, 0.075 g of HM-54, 0.068 g of HM-15, 0.090 g of HM-64 or 0.065 g of HM-27 and 0.057 g of HM-89 each behaving as a single component material by the electrophoresis with a polyacrylamide gel from the fractions F-0, F-I-1, F-I-2, F-II or F-III, respectively.

EXAMPLE 25

The first portion of the extraction procedure in Example 16 was repeated to give 42 g of a dry powdery product having a fibrinolytic activity for coagulated fibrin of 1322 mm$^2$/mg after fractional precipitation with ethyl alcohol and vacuum-drying. This powdery product was dissolved in 1 liter of purified water and the aqueous solution was fractionated by column chromatography with PEI-cellulose into five fractions of F-0, F-I-1, F-I-2, F-II and F-III containing novel proteases. Each of these fractions was further purified in substantially the same manner as in Example 17 to give 0.018 g of HM-45, 0.072 g of HM-54, 0.058 g of HM-15, 0.120 g of HM-64 or 0.066 g of HM-27 and 0.060 g of HM-89 each behaving as a single component pure material by the electrophoresis with a polyacrylamide gel from the fractions F-0, F-I-1, F-I-2, F-II or F-III, respectively.

EXAMPLE 26

The first portion of the extraction procedure in Example 16 was repeated to give 42 g of a dry powdery product having a fibrinolytic activity for coagulated fibrin of 1322 mm$^2$/mg after fractional precipitation with ethyl alcohol and vacuum-drying. This powdery product was dissolved in 1 liter of purified water and the aqueous solution was fractionated by column chromatography with AE-cellulose into five fractions of F-0, F-I-1, F-I-2, F-II and F-III. Each of these fractions was further purified in substantially the same manner as in Example 17 to give 0.022 g of HM-45, 0.072 g of HM-54, 0.064 g of HM-15, 0.100 g of HM-64 or 0.065 g of HM-27 and 0.056 g of HM-89 each behaving as a single component pure material by the electrophoresis with a polyacrylamide gel from the fractions F-0, F-I-1, F-I-2, F-II or F-III, respectively.

EXAMPLE 27

The first portion of the extraction procedure in Example 16 was repeated to give five fractions of F-0, F-I-1, F-I-2, F-II and F-III after the column chromatographic fractionation with DEAE-Cellulofine. Each of the fractions F-0, F-I-1, F-I-2 and F-II was further purified in substantially the same manner as in Example 17 to give 0.020 g of HM-45, 0.070 g of HM-54, 0.060 g of HM-15 and 0.100 g of HM-64, respectively, each behaving as a single component material by the electrophoresis with a polyacrylamide gel.

On the other hand, the eluate of the fraction F-III was passed through a column filled with a Sepharose affinity carrier bearing a soybean tryspin inhibitor (a product by PL Biochemicals, Inc.) and equilibrated in advance with a 20 mM phosphate buffer solution having a pH of 8.0 to have the active ingredients adsorbed thereon and, after washing with the same buffer solutions as above but additionally containing 1M of sodium chloride and then with 0.1M acetate buffer solution having a pH of 5.0, elution was performed with a 0.1M acetate buffer solution having a pH of 5.0 and containing 1M of arginine and 1M of sodium chloride to give an active fraction F-III$^1$. This fraction was further passed through a column of Biogel P-30 equilibrated with a saturated aqueous solution of ammonium sulfate to have the active ingredients adsorbed thereon followed by elution at a concentration gradient of 30% to 10% saturation with ammonium sulfate to give 0.060 g and 0.050 g of purified HM-27 and HM-89, respectively, each behaving as a single component material by the electrophoresis with a polyacryamide gel.

EXAMPLE 28

The first portion of the extraction procedure in Example 16 was repeated to give five fractions of F-0, F-I-1, F-I-2, F-II and F-III after the column chromatographic fractionation with DEAE-Cellulofine. Each of the fractions F-0, F-I-1, F-I-2 and F-II was further purified in substantially the same manner as in Example 17 to give 0.020 g of HM-45, 0.070 g of HM-54, 0.060 g of HM-15 and 0.100 g of HM-64, respectively, each behaving as a single component material by the electrophoresis with a polyacrylamide gel.

On the other hand, the fraction F-III was passed through a column filled with a Sepharose affinity carrier bearing a bacteria trypsin inhibitor (a product by Sigma Co.) and equilibrated in advance with a 20 mM phosphate buffer solution having a pH of 8.0 to have the active ingredients adsorbed thereon and, after washing with the same phosphate buffer solution but containing 1M of sodium chloride and then with a 0.1M acetate buffer solution having a pH of 5.0, elution was performed with a 0.1M acetate buffer solution having a pH of 5.0 and containing 1M of arginine and 1M of sodium chloride as an eluant to give an active fraction F-III$^1$. This fraction was further passed through a column filled with Toyopearl HW-55 equilibrated with a saturated aqueous solution of ammonium sulfate to have the active ingredients adsorbed thereon followed by elution at a concentration gradient of 30% to 10% saturation with ammonium sulfate to give each 0.050 g of purified HM-27 and HM-89 each behaving as a single component material by the electrophoresis with a polyacrylamide gel.

EXAMPLE 29

The first portion of the extraction procedure in Example 16 was repeated to give five fractions of F-0, F-I-1, F-I-2, F-II and F-III after column chromatographic fractionation. Each of these fractions except F-II was further purified in substantially the same manner as in Example 17 to give 0.020 g of HM-45, 0.070 g of HM-54, 0.060 g of HM-15 or 0.070 g of HM-27 and 0.060 g of HM-89 from the fraction F-0, F-I-1, F-I-2 or F-III, respectively, each behaving as a single component purified material by the electrophoresis with a polyacrylamide gel.

On the other hand, the fraction F-II was passed through a column filled with Toyopearl HW-55 (a product by Toyo Soda Co.) equilibrated in advance with an aqueous ammonium sulfate solution of 30% saturation to have the active ingredients adsorbed thereon followed by elution with a concentration gradient of 30% to 10% saturation with ammonium sulfate. The active fractions obtained in this elution were collected and, after desalting, passed through a column filled with octyl-Sepharose equilibrated in advance with a 10 mM phosphate buffer solution having a pH of 6.0 to have the active ingredients adsorbed thereon followed by elution with the same buffer solution at a concentration gradient of 0 to 0.5M of sodium chloride to have the active ingredients eluted out. The fractions containing the active ingredients were collected followed by gel filtration with Sephadex G-75 to give 0.070 g of HM-64 behaving as a single component purified material by the electrophoresis with a polyacrylamide gel.

EXAMPLE 30

The first portion of the extraction procedure of Example 16 was repeated to give five fractions of F-0, F-I-1, F-I-2, F-II and F-III after the column chromatographic fractionation. Each of the first three of these fractions was dissolved in a 10 mM phosphate buffer solution having a pH of 8.0 and the solution was passed through a column filled with DQAE-cellulose equilibrated in advance with the same buffer solution as above to have the active ingredients adsorbed thereon followed by elution at a concentration gradient of 0 to 10 mM of sodium chloride to give active fractions which were collected and purified in substantially the same manner as in Example 17 to give 0.018 g of HM-45, 0.060 g of HM-54 or 0.050 g of HM-15 from the fractions F-0, F-I-1 or F-I-2, respectively, each behaving as a single component purified material by the electrophoresis with a polyacrylamide gel.

The fraction F-II was purified in substantially the same manner as in Example 17 with gel filtration by use of Biogel P-100 (a product by Bio-Rad Co.) in the final step to give 0.090 g of HM-64 behaving as a single component purified material by the electrophoresis with a polyacrylamide gel.

On the other hand, the fraction F-III was purified in substantially the same manner as in Example 17 to give 0.068 g and 0.057 g of HM-27 and HM-89, respectively, each behaving as a single component purified material by the electrophoresis with a polyacrylamide gel.

EXAMPLE 31

The first portion of the extraction procedure in Example 16 was repeated to give five fractions of F-0, F-I-1, F-I-2, F-II and F-III after column chromatographic fractionation. Each of the first three of these fractions was passed through a column filled with EC-TEOLA-cellulose equilibrated in advance with a 10 mM phosphate buffer solution having a pH of 8.0 to have the active ingredients adsorbed thereon followed by elution at a concentration gradient of 0 to 100 mM with sodium chloride. The active fractions eluted out in this elution were collected and salted out by 60% saturation with ammonium sulfate. The precipitates obtained by the salting-out were dissolved in water and passed through a column filled with Toyopearl HW-55 equilibrated in advance with an equeous ammonium sulfate solution of 30% saturation to have the active ingredients adsorbed thereon followed by elution at a concentration gradient of 30% to 10% saturation with ammonium sulfate to give active fractions which were purified by desalting to give 0.021 g, 0.073 g and 0.065 g of HM-45, HM-54 and HM-15 from the fractions F-0, F-I-1 and F-I-2, respectively, each behaving as a single component purified material by the electrophoresis with a polyacrylamide gel.

The fraction F-II was further purified in substantially the same manner as in Example 17 except that the Sephadex G-75 in the gel filtration was replaced with Biogel P-30 to give 0.090 g of HM-64 behaving as a single component purified material by the electrophoresis with a polyacrylamide gel.

On the other hand, the fraction F-III was further purified in substantially the same manner as in Example 17 to give 0.068 g and 0.065 g of HM-27 and HM-89, respectively, each behaving as a single component purified material by the electrophoresis with a polyacrylamide gel.

What is claimed is:

1. White, amorphous and powdery protease F-III-1-HM-27 derived from earthworms, characterized by the properties and compositions of:

(A) enzymatic activities and substrate specificity comprising fibrinolytic activity against coagulated fibrin; plasminogen-activating activity; and strong activities to casein, tosyl-L-arginine methyl ester hydrochloride, chloride, N-α-tosyl-L-lysine methyl ester hydrochloride, L-pyroglutamylglycyl-L-arginine-p-nitroanilide hydrochloride and H-D-valyl-L-leucyl-L-lysine-p-nitroanilide dihydrochloride; but no activity to N-benzoyl-L-alanine methyl ester and N-benzoyl-L-tyrosine ethyl ester;

(B) an optimum pH at about 8 for the fibrinolysis with coagulated fibrin as the substrate and a pH of stability in the range from 5 to 12;

(C) an operable temperature in the range from 30° to 60° C. with an optimum temperature at about 50° C. in the fibrinolysis against coagulated fibrin at a pH of 7.8;

(D) complete deactivation by heating at 70° C. for 60 minutes;

(E) a molecular weight of 32,400±2,000;

(F) an ultraviolet absorption spectrum having a maximum absorption at about 280 nm and a minimum absorption at about 250 nm of the wavelength;

(G) an isoelectric point pI at a pH of 3.6±0.1;

(H) susceptibility to inhibitors including complete inhibition by lima bean trypsin inhibitor, difluorophosphate, soybean trypsin inhibitor, Antipain, Leupeptin and Trasylol; fairly strong inhibition by egg white trypsin inhibitor and trans-4-(aminomethyl)cyclohexane carboxylic acid; and weak inhibition by ε-aminocaproic acid, chimostatin and pepstatin; but substantially no inhibition by disodium ethylenediamine tetraacetate and N-ethylmaleimide in the fibrinolysis against coagulated fibrin;

(I) an amino acid composition of 15.25% of aspartic acid, 6.09% of threonine, 10.08% of serine, 7.04% of glutamic acid, 0.55% of proline, 12.66% of glycine, 6.90% of alanine, 1.36% of cystein, 10.33% of valine, 1.36% of methionine, 7.89% of isoleucine, 3.73% of leucine, 4.63% of tyrosine, 3.09% of phenylalanine, 0.83% of tryptophan, 1.65% of lysine, 2.37% of histidine and 4.19% of arginine, each % being by moles involving an unavoidable analytical error; and (J) an elementary composition of 48.61% of carbon, 6.58% of hydrogen, 14.75% of nitrogen and 2.03% of sulfur, each % being by weight involving an unavoidable analytical error.

2. White, amorphous and powdery protease F-0-HM-45 derived from earthworms, characterized by the properties and compositions of:

(A) enzymatic activities and substrate specificity comprising fibrinolytic activity against coagulated fibrin; plasminogen-activating activity; and strong activities to casein, tosyl-L-arginine methyl ester hydrochloride and N-benzoyl-L-tyrosine ethyl ester; and very weak activities to L-pyroglutamylglycyl-L-arginine-p-nitroanilide hydrochloride and H-D-valyl-L-leucyl-L-lysine-p-nitroanilide dihydrochloride; but almost no activities to N-α-tosyl-L-lysine methyl ester hydrochloride and N-benzyl-L-alanine methyl enter;

(B) an optimum pH in the range from about 8 to about 10 for the fibrinolysis with coagulated fibrin is the substrate and a pH of stability in the range from 4 to 12;

(C) an operable temperature in the range from 30° to 60° C. with an optimum temperature in the range from about 50° to about 60° C. in the fibrinolysis against coagulated fibrin at a pH of 7.8;

(D) complete deactivation by heating at 70° C. for 60 minutes;

(E) a molecular weight of 24,500±2,000;

(F) an ultraviolet absorption spectrum having a maximum absorption at about 280 nm and a minimum absorption at about 250 nm of the wavelength;

(G) an isoelectric point pI at a pH of 4.1±0.1;

(H) susceptibility to inhibitors including complete inhibition by lima bean trypsin inhibitor, difluorophosphate, soybean trypsin inhibitor, Antipain, Leupeptin, Trasylol and chimostatin; fairly strong inhibition by trans-4-(aminomethyl)cyclohexane carboxylic acid and ε-aminocaproic acid; weak inhibition by egg white trypsin inhibitor, pepstatin and N-ethylmaleimide; but substantially no inhibition by disodium ethylenediamine tetraacetate in the fibrinolysis against coagulated fibrin;

(I) an amino acid composition of 12.26% of aspartic acid, 12.22% of threonine, 9.38% of serine, 3.97% of glutamic acid, 0.40% of proline, 13.48% of glycine, 12.95% of alanine, 1.44% of cystein, 7.03% of valine, 0.55% of methionine, 5.83% of isoleucine, 7.47% of leucine, 3.91% of tyrosine, 2.00% of phenylalanine, 0.64% of tryptophan, 0.04% of lysine, 2.45% of histidine and 3.98% of arginine, each % being by moles involving an unavoidable analytical error; and (J) an elementary composition of 48.30% of carbon, 6.84% of hydrogen, 15.88% of nitrogen and 2.07% of sulfur, each % being by weight involving an unavoidable analytical error.

3. White, amorphous and powdery protease F-I-1-HM-54 derived from earthworms characterized by the properties and compositions of:

(A) enzymatic activities and substrate specificity comprising fibrinolytic activity against coagulated fibrin; plasminogen-activating activity; and strong activities to casein, tosyl-L-arginine methyl ester hydrochloride and N-benzoyl-L-tyrosine ethyl ester; and very weak activities to N-α-tosyl-L-lysine methyl ester hydrochloride and L-pyroglutamylglycyl-L-arginine-p-nitroanilide hydrochloride; but almost no activities to H-D-valyl-L-leucyl-L-lysine-p-nitroanilide dihydrochloride and N-benzyl-L-alanine methyl ester;

(B) an optimum pH in the range from about 8 to about 10 for the fibrinolysis with coagulated fibrin as the substrate and a pH of stability in the range from 4 to 12;

(C) an operable temperature in the range from 30° to 60° C. with an optimum temperature in the range from about 50° to about 60° C. in the fibrinolysis against coagulated fibrin at a pH of 7.8;

(D) complete deactivation by heating at 70° C. for 60 minutes;

(E) a molecular weight of 27,500±2,000;

(F) an ultraviolet absorption spectrum having a maximum absorption at about 280 nm and a minimum absorption at about 250 nm of the wavelength;

(G) an isoelectric point pI at a pH of 4.0±0.1;

(H) susceptibility to inhibitors including complete inhibition by lima bean trypsin inhibitor, difluorophosphate and N-ethylmaleimide; fairly strong inhibition by soybean trypsin inhibitor and Leupeptin; and weak inhibition by egg white trypsin inhibitor, trans-4-(aminomethyl)cyclohexane carboxylic acid and chimostatin; but no inhibition by Antipain, Trasylol, ε-aminocaproic acid, pepstatin and disodium ethylenediamine tetraacetate in the fibrinolysis against coagulated fibrin;

(I) an amino acid composition of 15.65% of aspartic acid, 8.25% of threonine, 11.30% of serine, 6.05% of glutamic acid, 0.37% of proline, 15.39% of glycine, 9.49% of alanine, 1.09% of cystein, 5.46% of valine, 0.97% of methionine, 6.54% of isoleucine, 7.95% of leucine, 3.69% of tyrosine, 1.11% of phenylalanine, 0.98% of tryprophan, 0.50% of lysine, 2.75% of histidine and 2.46% of arginine, each % being by moles involving an unavoidable analytical error; and (J) an elementary composition of 48.93% of carbon, 6.65% of hydrogen, 15.95% of nitrogen and 1.34% of sulfur, each % being by weight involving an unavoidable analytical error.

4. White, amorphous and powdery protease F-I-2-HM-15 derived from earthworms characterized by the properties and compositions of:

(A) enzymatic activities and substrate specificity comprising fibrinolytic activity against coagulated fibrin; plasminogen-activating activity; and strong activities to casein, tosyl-L-arginine methyl ester hydrochloride and N-benzoyl-L-tyrosine ethyl ester; and very weak activities to N-α-tosyl-L-lysine methyl ester hydrochloride and L-pyroglutamylglycyl-L-arginine-p-nitroanilide hydrochloride; but almost no activities to H-D-valyl-L-leucyl-L-lysine-p-nitroanilide dihydrochloride and N-benzoyl-L-alanine methyl ester;

(B) an optimum pH in the range from about 8 to about 10 for the fibrinolysis with coagulated fibrin as the substrate and a pH of stability in the range from 4 to 12;

(C) an operable temperature in the range from 30° to 60° C. with an optimum temperature in the range from about 50° to about 60° C. in the fibrinolysis against coagulated fibrin at a pH of 7.8;

(D) complete deactivation by heating at 70° C. for 60 minutes;

(E) a molecular weight of 27,000±2,000;

(F) an ultraviolet absorption spectrum having a maximum absorption at about 280 nm and a minimum absorption at about 250 nm of the wavelength;

(G) an isoelectric point pI at a pH of 3.9±0.1;

(H) susceptibility to inhibitors including complete inhibition by lima bean trypsin inhibitor, difluorophosphate and N-ethylmaleimide; fairly strong inhibition by Leupeptin and egg white trypsin inhibitor; and weak inhibition by soybean trypsin inhibitor, Antipain, trans-4-(aminomethyl)cyclohexane carboxylic acid, ε-aminocaproic acid, chimostatin, pepstatin and disodium ethylenediamine tetraacetate; but no inhibition by Trasylol in the fibrinolysis against coagulated fibrin;

(I) an amino acid composition of 16.06% of aspartic acid, 8.46% of threonine, 10.85% of serine, 6.13% of glutamic acid, 0.41% of proline, 15.41% of glycine, 9.45% of alanine, 1.67% of cystein, 5.51% of valine, 0.82% of methionine, 6.64% of isoleucine, 8.01% of leucine, 3.79% of tyrosine, 1.11% of phenylalanine, undetectable amount of tryptophan, 0.53% of lysine, 2.73% of histidine and 2.42% of arginine, each % being by moles involving an unavoidable analytical error; and (J) an elementary composition of 46.15% of carbon, 6.64% of hydrogen, 16.02% of nitrogen and 2.05% of sulfur, each % being by weight involving an unavoidable analytical error.

5. White, amorphous and powdery protease F-II-HM-64 derived from earthworms characterized by the properties and compositions of:
(A) enzymatic activities and substrate specificity comprising fibrinolytic activity against coagulated fibrin; plasminogen-activating activity; and strong activities to casein; good activities to tosyl-L-arginine methyl ester hydrochloride; weak activities to N-α-tosyl-L-lysine methyl ester hydrochloride and L-pyroglutamylglycyl-L-arginine-p-nitroanilide hydrochloride; and very weak activities to H-D-valyl-L-leucyl-L-lysine-p-nitroanilide dihydrochloride; but almost no activity to N-benzoyl-L-alanine methyl ester and N-benzoyl-L-tyrosine ethyl ester;
(B) an optimum pH in the range from about 7 to about 8 for the fibrinolysis with coagulated fibrin as the substrate and a pH of stability in the range from 5 to 12;
(C) an operable temperature in the range from 30° to 60° C. with an optimum temperature in the range from about 50° to about 60° C. in the fibrinolysis against coagulated fibrin at a pH of 7.8;
(D) complete deactivation by heating at 70° C. for 60 minutes;
(E) a molecular weight of 27,800±2,000;
(F) an ultraviolet absorption spectrum having a maximum absorption at about 280 nm and a minimum absorption at about 250 nm of the wavelength;
(G) an isoelectric point pI at a pH of 3.8±0.1;
(H) susceptibility to inhibitors including complete inhibition by lima bean trypsin inhibitor, difulorophosphate, soybean trypsin inhibitor and N-ethylmaleimide, fairly strong inhibition by Trasylol, egg white trypsin inhibitor, trans-4-(aminomethyl)cyclohexane carboxylic acid, chimostatin and pepstatin; and weak inhibition by Antipain and ⊖-aminocaproic acid; but no inhibition by Leupeptin and disodium ethylenediamine tetraacetate in the fibrinolysis against coagulated fibrin;
(I) an amino acid composition of 14.81% of aspartic acid, 8.40% of threonine, 12.05% of serine, 6.04% of glutamic acid, 0.44% of proline, 14.48% of glycine, 10.27% of alanine, 0.80% of cystein, 7.77% of valine, 0.98% of methionine, 5.96% of isoleucine, 7.46% of leucine, 3.24% of tyrosine, 0.58% of phenylalanine, 1.63% of tryptophan, 0.45% of lysine, 2.30% of histidine and 2.34% of arginine, each % being by moles involving an unavoidable analytical error; and
(J) an elementary composition of 48.23% of carbon, 6.53% of hydrogen, 15.93% of nitrogen and 1.43% of sulfur, each % being by weight involving an unavoidable analytical error.

6. White, amorphous and powdery protease F-III-2-HM-89 derived from earthworms characterized by the properties and compositions of:
(A) enzymatic activities and substrate specificity comprising fibrinolytic activity against coagulated fibrin; plasminogen-activating activity; and good activities to casein, tosyl-L-arginine methyl ester hydrochloride, N-α-tosyl-L-lysine methyl ester hydrochloride, L-pyroglutamylglycyl-L-arginine-p-nitroanilide hydrochloride and H-D-valyl-L-leucyl-L-lysine-p-nitroanilide dihydrochloride; but almost no activity to N-benzoyl-L-alanine methyl ester and N-benzoyl-L-tyrosine ethyl ester;
(B) an optimum pH at about 8 for the fibrinolysis with coagulated fibrin as the substrate and pH of stability in the range from 4 to 12;
(C) an operable temperature in the range from 30° to 60° C. with an optimum temperature in the range from about 50° to about 60° C. in the fibrinolysis against coagulated fibrin at a pH of 7.8;
(D) complete deactivation by heating at 70° C. for 60 minutes;
(E) a molecular weight of 32,800±2,000;
(F) an ultraviolet absorption spectrum having a maximum absorption at about 280 nm and a minimum absorption at about 250 nm of the wavelength;
(G) an isoelectric point pI at a pH of 3.5±0.1;
(H) susceptibility to inhibitors including complete inhibition by lima bean trypsin inhibitor, difluorophosphate, soybean trypsin inhibitor, Antipain, Leupeptin and Trasylol; fairly strong inhibiton by trans-4-(aminomethyl) cyclohexane carboxylic acid; and weak inhibition by egg white trypsin inhibitor, ε-aminocaproic acid, chimostatin and pepstatin, but no inhibition by disodium ethylenediamine tetraacetate and N-ethylmaleimide in the fibrinolysis against coagulated fibrin;
(I) an amino acid composition of 14.99% of aspartic acid, 6.24% of threonine, 10.39% of serine, 7.63% of glutamic acid, 0.57% of proline, 12.89% of glycine, 6.57% of alanine, 1.40% of cystein, 10.67% of valine, 1.34% of methionine, 7.62% of isoleucine, 3.41% of leucine, 4.83% of tyrosine, 2.67% of phenylalanine, 1.09% of tryptophan, 1.67% of lysine, 2.12% of histidine and 3.90% of arginine, each % being by moles involving an unavoidable analytical error; and
(J) an elementary composition of 47.53% of carbon, 6.55% of hydrogen, 14.59% of nitrogen and 2.06% of sulfur, each % being by weight involving an unavoidable analytical error.

7. A thrombolytically active enzyme material derived from earthworms which comprises, as the active ingredient thereof, at least one of the proteases selected from the class consisting of proteases F-0-HM-45, F-I-1-HM-54, F-I-2-HM-15, F-II-HM-64, F-III-1-HM-27 and F-III-2-HM-89.

8. A method for the preparation of fibrinolytically active proteases F-0-HM-45, F-I-1-HM-54 and F-I-2-HM-15 which comprises the successive steps of:
(a) extracting earthworm tissues with an aqueous extractant to give an extract solution containing the proteases;
(b) adding a polar organic solvent to the extract solution to give precipitates containing the proteases;
(c) fractionating the precipitates by anion-exchange chromatography into five fibrinolytically active fractions, three of which contain each one of the proteases F-0-HM-45, F-I-1-HM-54 and F-I-2-HM-15;
(d) passing each of the fractions each containing one of the proteases F-0-HM-45, F-I-1-HM-54 and F-I-2-HM-15 through a column filled with an anion exchanger to have the active ingredients adsorbed thereon;
(e) eluting out the active ingredients adsorbed on each of the anion exchangers in the step (d) by the method of concentration gradient with sodium chloride to give a fraction containing one of the proteases F-0-HM-45, F-I-1-HM-54 and F-I-2-HM-15; and (f) purifying each of the fractions containing the protease F-0-HM-45, F-I-1-HM-54 or F-I-2-HM-15 by use of a gel ion exchanger.

9. The method as claimed in claim 8 wherein the step (f) is performed by passing the fraction through a column filled with a gel ion exchanger to have the active ingredient adsorbed thereon followed by elution of the active ingredient by the method of concentration gradient with ammonium sulfate and then desalting the eluate solution.

10. A method for the preparation of a fibrinolytically active protease F-II-HM-64 which comprises the successive steps of:
(a) extracting earthworm tissues with an aqueous extractant to give an extract solution containing the protease;
(b) adding a polar organic solvent to the extract solution to give precipitates containing the protease;
(c) fractionating the precipitates by anion-exchange chromatography into five fibrinolytically active fractions, one of which contains the protease F-II-HM-64;
(d) passing the fraction containing the protease F-II-HM-64 through a column filled with a gel ion exchanger to have the active ingredient adsorbed thereon;
(e) eluting the active ingredient by the method of concentration gradient with ammonium sulfate to give a fraction containing the protease F-II-HM-64;
(f) desalting the fraction containing the protease;
(g) passing the desalted fraction through a column filled with an adsorbent for affinity chromatography to have the active ingredient adsorbed thereon;
(h) eluting the active ingredient by the method of concentration gradient with sodium chloride to give a fraction containing the protease F-II-HM-64; and
(i) purifying the fraction containing the protease F-II-HM-64 by use of a gel ion exchanger.

11. A method for the fractionating preparation of fibrinolytically active proteases F-III-1-HM-27 and F-III-2-HM-89 which comprises the successive steps of:
(a) extracting earthworm tissues with an aqueous extractant to give an extract solution containing the proteases;
(b) adding a polar organic solvent to the extract solution to give precipitates containing the proteases;
(c) fractionating the precipitates by anion-exchange chromatography into five fibrinolytically active fractions, one of which contains the proteases F-III-1-HM-27 and F-III-2-HM-89;
(d) purifying the fraction containing the proteases by the method of affinity chromatography;
(e) passing the affinity-chromatographically purified fraction in the step (d) through a column filled with a gel ion exchanger to have the proteases adsorbed thereon;
(f) eluting the proteases by the method of concentration gradient with ammonium sulfate to give fractions each containing the protease F-III-1-HM-27 or F-III-2-HM-89; and
(g) desalting the fractions containing the proteases.

12. A method for the fractionating preparation of fibrinolytically active enzyme materials each mainly composed of protease F-0-HM-45, F-I-1-HM-54, F-I-2-HM-15, F-II-HM-64 or a mixture of F-III-1-HM-27 and F-III-2-HM-89 which comprises the successive steps of:
(a) extracting earthworm tissues with an aqueous extractant to give an extract solution containing the proteases;
(b) adding a polar organic solvent to the extract solution to give precipitates containing the proteases;
(c) fractionating the precipitates by anion-exchange chromatography into five fibrinolytically active fractions each containing at least one of the proteases;
(d) subjecting each of the fractions to salting-out to give precipitates containing the proteases;
(e) dissolving the precipitates in a buffer solution to give a solution;
(f) subjecting the solution to gel filtration; and
(g) desalting and concentrating the gel-filtrated solution by ultrafiltration.

13. A thrombolytic medicament form which comprises at least one of the proteases derived from earthworms, and selected from the class consisting of proteases F-0-HM-45, F-I-1-HM-54, F-I-2-HM-15, F-II-HM-64, F-III-1-HM-27 and F-III-2-HM-89 as the effective ingredient in a therapeutically effective amount and at least one physiologically acceptable carrier.

14. The thrombolytic medicament form as claimed in claim 13 wherein the carrier is physiologically acceptable by oral administration.

15. A method for therapeutically treating a human patient suffering thrombosis which comprised administering the patient with an effective amount of a thrombolytic medicament form containing, as an effective ingredient thereof, at least one protease derived from earthworms selected from the class consisting of protease F-III-1-HM-27, protease F-III-2-HM-89, protease F-0-HM-45, protease F-I-1-HM-54, protease F-I-2-HM-15, protease F-II-HM-64, proteas F-III$^1$, protease F-II$^1$, protease F-I$^1$ and protease F-I$^2$, wherein protease F-III$^1$ is a composite of proteases F-III-1-HM-27 and F-III-2-HM-89, protease F-II$^1$ is a composite of proteases F-I-1-HM-54 and F-I-2-HM-15, protease F-I$^1$ is a composite of proteases F-0-HM-45, F-I-1-HM-54 and F-I-2-HM-15, proteases F-I$^2$ is a protease composed mainly of protease F-II-HM-64.

* * * * *